United States Patent
Mine et al.

(10) Patent No.: US 8,123,691 B2
(45) Date of Patent: Feb. 28, 2012

(54) ULTRASONIC DIAGNOSTIC APPARATUS FOR FIXEDLY DISPLAYING A PUNCTURE PROBE DURING 2D IMAGING

(75) Inventors: Yoshitaka Mine, Nasu-gun (JP); Hitoshi Yamagata, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 10/920,240

(22) Filed: Aug. 18, 2004

(65) Prior Publication Data

US 2005/0090742 A1   Apr. 28, 2005

(30) Foreign Application Priority Data

Aug. 19, 2003 (JP) .................................. 2003-294925
May 12, 2004 (JP) .................................. 2004-142383

(51) Int. Cl.
 *A61B 8/12* (2006.01)
(52) U.S. Cl. ....................................................... 600/439
(58) Field of Classification Search .................. 600/439, 600/424, 101, 437, 440, 445, 459, 462, 463, 600/464
See application file for complete search history.

(56) References Cited

U.S. PATENT DOCUMENTS

| | | | | |
|---|---|---|---|---|
| 5,255,680 A * | 10/1993 | Darrow et al. | ................ | 600/424 |
| 5,660,185 A * | 8/1997 | Shmulewitz et al. | ......... | 600/562 |
| 6,048,312 A * | 4/2000 | Ishrak et al. | .................. | 600/443 |
| 6,119,033 A * | 9/2000 | Spigelman et al. | ............ | 600/426 |
| 6,216,029 B1 * | 4/2001 | Paltieli | .......................... | 600/427 |
| 6,246,898 B1 * | 6/2001 | Vesely et al. | .................. | 600/424 |
| 6,529,766 B1 * | 3/2003 | Guendel | ........................ | 600/427 |
| 6,733,458 B1 * | 5/2004 | Steins et al. | ................... | 600/461 |

FOREIGN PATENT DOCUMENTS

| | | |
|---|---|---|
| JP | 63-290550 | 11/1988 |
| JP | 2000-107178 | 4/2000 |
| WO | WO 97/03609 | 2/1997 |

OTHER PUBLICATIONS

Moriyasa, et al., "Practical Radio-Wave Thermocoagulation Therapy of Hepatic Cancer", May 2002, (22 pages).

* cited by examiner

*Primary Examiner* — Parikha Mehta
(74) *Attorney, Agent, or Firm* — Oblon, Spivak, McClelland, Maier & Neustadt, L.L.P.

(57) ABSTRACT

Ultrasonic diagnostic equipment is equipped with an ultrasonic probe that transmits/receives ultrasound to/from an examined body, a probe position sensor that detects the position and the direction of the ultrasonic probe, an image generator that generates image data based upon the output of the ultrasonic probe, a probe position sensor that detects the position and the direction of a puncture probe inserted into the examined body, a display image generator that generates the data of a display image in which the end position of the puncture probe is fixed to a specific position in an image display area according to the position and the direction of the ultrasonic probe and the position and the direction of the puncture probe based upon the image data and a display for displaying the display image in the image display area.

15 Claims, 17 Drawing Sheets

ULTRASONIC DIAGNOSTIC APPARATUS FOR FIXEDLY DISPLAYING A PUNCTURE PROBE DURING 2D IMAGING

CROSS-REFERENCE TO RELATED APPLICATIONS

This application is based upon and claims the benefit of priority from prior Japanese Patent Applications No. 2003-294925, filed Aug. 19, 2003; and No. 2004-142383, filed May 12, 2004, the entire contents of both of which are incorporated herein by reference.

BACKGROUND OF THE INVENTION

1. Field of the Invention

The present invention relates to ultrasonic diagnostic equipment for guiding the insertion of a puncture probe or a treatment probe such as a PEIT probe, a radio frequency puncture probe and a microwave puncture probe into a target part.

2. Description of the Related Art

For treatment for a tumor such as a cancer of an internal organ, a puncture probe or a treatment probe is often inserted into a target part by ultrasonic guidance and the insertion is called ultrasonically guided puncture and others.

In case these probes are inserted, a guide mechanism for setting the insertion direction of the puncture probe for an ultrasonic probe of used ultrasonic diagnostic equipment is provided or a puncture adaptor is installed so that these probes are located in the diagnostic visual field of the ultrasonic diagnostic equipment for insertion. On the screen of the ultrasonic diagnostic equipment, the insertion path of the puncture probe preset in the guide mechanism or the puncture adaptor is displayed beforehand, is referred as an index, is located in a target part, and operation for the insertion of the puncture probe is executed.

Cells in the target part are extracted by the inserted puncture probe or cancer coagulation treatment in which ethanol is injected into the target part via the puncture probe is made. Recently, cancer cauterization treatment in which a microwave or a radio wave is radiated and the puncture probe for cauterization for cauterizing cancer is inserted may be also made (for example, refer to "Actual liver cancer radio frequency thermocoagulation therapy" compiled by Kokubu and Moriyasu and published by Nankodo in May, 2002).

As in insertion under ultrasonic guidance, a puncture probe is thin and the insertion direction is substantially parallel to an ultrasonic beam from ultrasonic diagnostic equipment at a small angle, a reflected wave signal having sufficient intensity by the probe cannot be acquired, and the stable and clear display on an ultrasonotomographic image of the position of the probe may be disabled.

In a process of insertion, the end of the puncture probe is bent in a direction having little resistance because of the resistance of internal organs and tissue, is inserted off from the width in a direction (also called a slice) of a tomographic image by an ultrasonic beam, and no puncture probe exists on an ultrasonotomographic layer. Further, as internal organs and tissue are moved by respiration, the puncture probe may be off an ultrasonic beam which is a field of view after insertion.

The invention for intensifying a reflected signal the sufficient intensity of which cannot be acquired (for example, refer to JP-A-63-290550) and the invention for adjusting an ultrasonic beam to a puncture probe off a field of view (for example, refer to JP-A-2000-107178) are proposed.

However, an ultrasonotomographic image by the puncture probe under the above-mentioned ultrasonic guidance cannot be sufficiently observed, operation for insertion into a target part is very difficult, and insufficiency in the stability of display and operability comes into question.

In treatment under ultrasonic guidance, positional relation among a tumor, a blood vessel, ambient internal organs and positional relation with the ends of probes are observed, moving probes in various positions on the surface of the body. Particularly, in cautery treatment by a radio wave and a microwave under ultrasonic guidance, progress is required to be observed during the treatment.

Besides, there is also a problem that the observation of a part at the back of a cauterized part from the position of a probe over a treated part is disabled because of the alteration of tissue by cauterization and generated bubbles. Therefore, a puncture adaptor is detached from a probe during treatment, a puncture probe and the probe are detached, and internal organs and tissue including the circumference of a target part are scanned by the probe and are often observed from a desired direction.

Therefore, in treatment under ultrasonic guidance, the three-dimensional grasping and verification of a target part and a treated part are important. However, in treatment using the ultrasonic diagnostic equipment depending upon only the above-mentioned guide mechanism of the conventional type puncture probe and the puncture adaptor, it comes into a large question that observation is enabled in only a direction in which the puncture probe related to the treatment is maintained in the slice width of an ultrasonic beam and the three-dimensional positional grasping is difficult.

Besides, as described above, to treat a tumor such as cancer of an internal organ, a puncture probe is often inserted into a target part of an examined body under the guidance of a tomographic image by ultrasonic diagnostic equipment. In such a case, a guide mechanism for setting the insertion direction of the puncture probe is provided to a probe of the used ultrasonic diagnostic equipment or a puncture adaptor is installed on the probe, and the puncture probe is inserted so that it is located in a diagnostic visual field by the ultrasonic diagnostic equipment. On the screen of the ultrasonic diagnostic equipment, the insertion path of the puncture probe which is preset in the guide mechanism and the puncture adaptor is displayed beforehand, is referred as an index, is located in a target part and operation for inserting the puncture probe is executed.

Cells in the target part are extracted by the inserted puncture probe and cancer coagulation treatment in which ethanol is injected into the target part via the puncture probe is made. Recently, to radiate a microwave and a radio wave and cauterize cancer, a puncture probe for cauterization is inserted and treatment for cancer may be made. Cautery by a radio wave is described in "Actual liver cancer radio frequency thermocoagulation therapy" compiled by Kokubu and Moriyasu and published by Nankodo in May, 2002 for example.

In case the puncture probe is inserted, viewing a tomographic image by ultrasonic diagnostic equipment, there is a problem that a reflected wave having sufficient intensity by the puncture probe cannot be acquired and the stable and clear display of the position of the probe in the ultrasonotomographic image is difficult because the puncture probe is thin, the insertion direction is substantially parallel to an ultrasonic beam at a small angle.

Besides, the end of the puncture probe is bent in a direction having little resistance of internal organs and tissue in a process of insertion, is off the width in a tomographic image direction (a slice direction) of an ultrasonic beam, no puncture probe exists on an ultrasonotomographic layer, the puncture probe is off the ultrasonic beam after insertion because internal organs and tissue are moved by respiration, and may be even invisible.

Then, some methods of making a puncture probe clear are known and ultrasonic diagnostic equipment for acquiring three-dimensional data is being developed. This type of equipment executes three-dimensional scanning by executing three-dimensional electronic ultrasonographic scanning or mechanically moving a probe and as three-dimensional volume data can be collected, a tomographic layer on which a puncture probe exists can be displayed by such equipment.

As described above, in three-dimensional ultrasonographic diagnostic equipment, predetermined volume is displayed at real time and designated plural tomographic layers are also displayed. However, a method of following an inserted puncture probe and displaying the end of the probe is not established yet.

As described in JP-A-2000-185041 for example, ultrasonic diagnostic equipment in which a signal generator is installed at the end of a puncture probe, a signal from this is received by at least three ultrasonic transducers and the end position of the puncture probe is estimated is known.

However, in this equipment, the signal generator is required to be provided to the end of the puncture probe, the puncture probe is required to be as thin as possible, and the signal generator is also required to be miniaturized. However, when the signal generator is miniaturized, signals received by the three ultrasonic transducers are reduced, and it is difficult to estimate the end position of the puncture probe.

Even if the end position of the puncture probe can be estimated in such a structure, only the current position of the end of the puncture probe can be actually detected. Prior to puncture, it is important where and in which direction puncture is made. However, in the above-mentioned conventional type ultrasonic diagnostic equipment, it is difficult to know a traveling direction of the end of the puncture probe which is the most important.

Besides, in case a puncture probe is inserted from an optimum position on the surface of the body without utilizing a puncture adaptor and the puncture adaptor has a degree of freedom in the inserted position and the inserted angle of the puncture probe, a path in which the puncture probe is inserted cannot be estimated. Besides, it cannot be estimated whether the puncture probe can reach a target part or not.

As described above, according to the conventional type ultrasonic diagnostic equipment for assisting puncture, the end position of the puncture probe cannot be precisely detected and a direction in which the puncture probe is inserted cannot be known.

BRIEF SUMMARY OF THE INVENTION

The object of the invention is to provide ultrasonic diagnostic equipment that also catches a therapeutic puncture probe in a part except the slice width of an ultrasonic beam and three-dimensionally displays an ultrasonotomographic image for observation, that is, the position of the puncture probe for an internal organ and cancer to be treated.

Another object of the invention is to provide clinically useful ultrasonic diagnostic equipment for assisting puncture wherein the end position of a puncture probe can be easily detected, a direction in which the puncture probe is inserted can be detected and further, the vicinity of a detected puncture path is scanned or is imaged in reconstruction to three-dimensionally monitor the puncture probe.

According to a first aspect of the present invention, there is provided ultrasonic diagnostic equipment equipped with an ultrasonic probe that transmits/receives ultrasonic to/from an examined body, a probe position sensor that detects the position and the direction of the ultrasonic probe, an image generator that generates image data based upon the output of the ultrasonic probe, a puncture probe position sensor that detects the position and the direction of a puncture probe inserted into the examined body, a display image generator that generates the data of a display image in which the end position of the puncture probe is fixed to a specific position in an image display area according to the detected position and direction of the ultrasonic probe and the detected position and direction of the puncture probe based upon the image data and a display that displays the display image in the image display area.

According to a second aspect of the present invention, there is provided ultrasonic diagnostic equipment equipped with an ultrasonic probe that transmits/receives ultrasonic to/from an examined body, a probe position sensor that detects the position and the direction of the ultrasonic probe, a tomographic image generator that generates the data of a tomographic image based upon the output of the ultrasonic probe, a puncture probe position sensor that detects the position and the direction of a puncture probe inserted into the examined body and a controller that controls the transmission/reception of the ultrasonic probe to scan a layer including the puncture probe or an insertion estimated path or a layer in the vicinity with ultrasonic based upon the detected position and direction of the ultrasonic probe and the detected position and direction of the puncture probe.

According to a third aspect of the present invention, there is provided ultrasonic diagnostic equipment equipped with an ultrasonic probe that transmits/receives ultrasonic to/from an examined body, a probe position sensor that detects the position and the direction of the ultrasonic probe, a tomographic image generator that generates the data of a tomographic image based upon the output of the ultrasonic probe, a puncture probe position sensor that detects the position and the direction of a puncture probe inserted into the examined body and a controller that controls the transmission/reception of the ultrasonic probe to scan a layer crossed with the end of the puncture probe or a layer in the vicinity with ultrasonic based upon the detected position and direction of the ultrasonic probe and the detected position and direction of the puncture probe.

Additional objects and advantages of the invention will be set forth in the description which follows, and in part will be obvious from the description, or may be learned by the practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
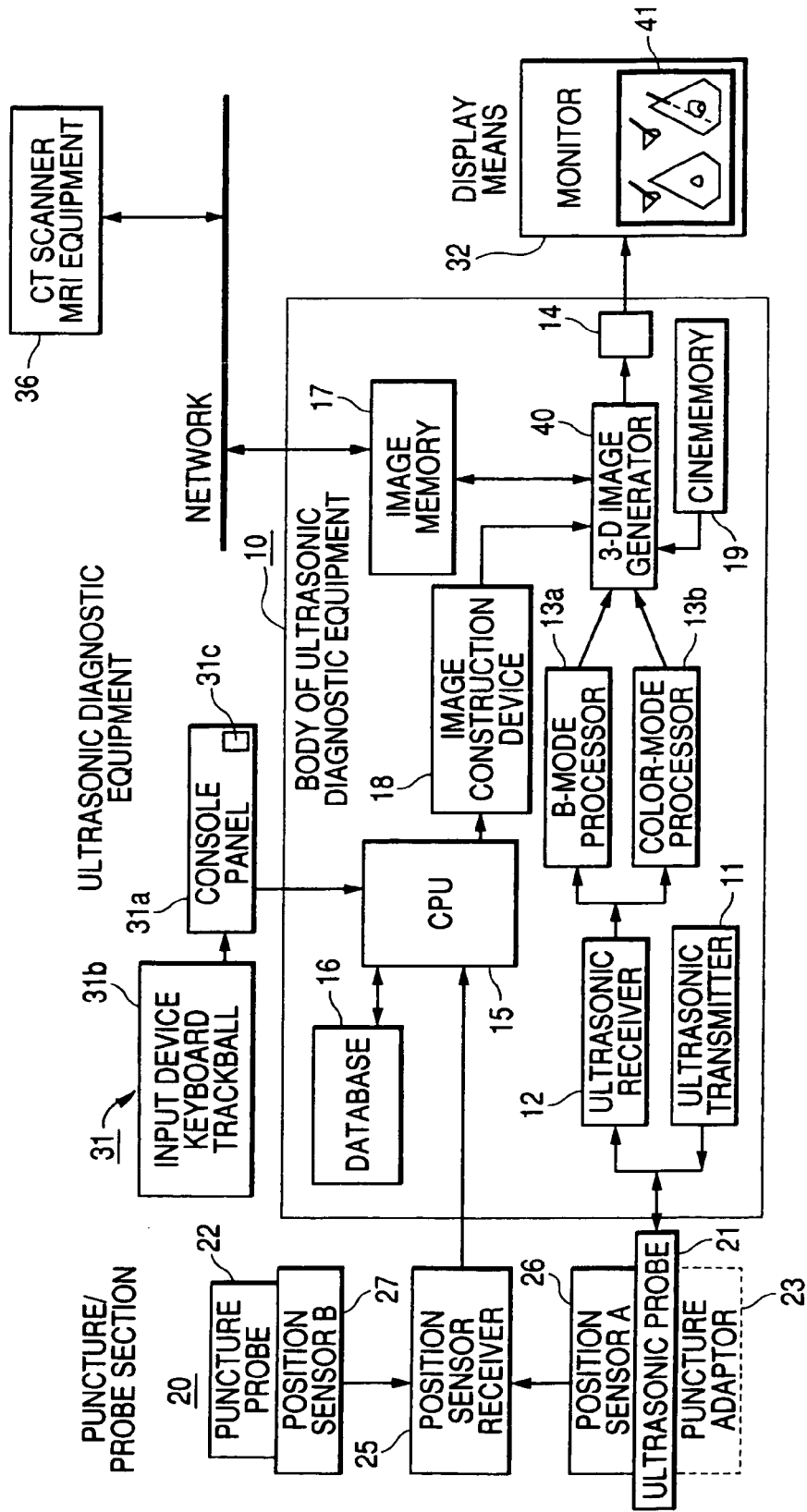
FIG. 1 is a block diagram showing a 1-1 embodiment of ultrasonic diagnostic equipment according to the invention.

Referring to the drawings, embodiments of the invention will be described in detail below.

1-1 Embodiment

FIG. 1 is a block diagram showing a 1-1 embodiment of ultrasonic diagnostic equipment according to the invention.

Ultrasonic diagnostic equipment equivalent to this embodiment is composed of the body 10 of the ultrasonic diagnostic equipment that processes an ultrasonic signal and outputs a picture signal, a puncture/probe section 20 including an ultrasonic probe 21 and a puncture probe 22 respectively provided with a position sensor, input means 31 for operating the body 10 of the ultrasonic diagnostic equipment and a monitor 32 that displays the picture signal.

The body 10 of the ultrasonic diagnostic equipment is composed of an ultrasonic transmitter 11, an ultrasonic receiver 12, a B-mode processor 13a, a color-mode processor 13b, a three-dimensional image generator 40, a display output device 14, CPU 15 for control and arithmetic processing, a database 16, an image memory 17, an image construction device 18 and a cinememory 19 that stores a dynamic image. The three-dimensional image generator 40 selectively generates data for a two-dimensional display image in which the end position of the puncture probe 22 is fixed to a specific position in an image display area, typically the center of the image display area according to the detected position and direction of the ultrasonic probe 21 and those of the puncture probe 22 or data for a two-dimensional display image in which the fixing is released based upon the data (volume data) of multilevel tomographic images.

The puncture/probe section 20 is composed of the ultrasonic probe 21 which is connected to the ultrasonic transmitter 11 and the ultrasonic receiver 12 and to which a position sensor A 26 is attached so that it can be detached, the puncture probe 22 to which a position sensor B 27 is attached so that it can be detached and a position sensor receiver 25 that receives a positional signal and a directional signal from the position sensor A 26 and the position sensor B 27 and outputs positional data to connected CPU 15. A puncture adaptor 23 is provided to the ultrasonic probe 21 so that the puncture adaptor can be detached.

The input means 31 for operating the body 10 of the ultrasonic diagnostic equipment is composed of a console panel 31a provided with function keys for selecting a function and instructing operation and a fixing/release button 31c of a probe end display position and an input device 31b such as a keyboard and a trackball.

While the fixing/release button 31c is pressed, the end position of the puncture probe 22 is fixed to the specific position on the screen of the monitor 32, typically the center of the image display area 41. That is, a display image is generated so that the end position of the puncture probe 22 is coincident with the center of the image display area 41. When plural image display areas 41 are provided, a display image is generated so that the end position of the puncture probe 22 is coincident with each center of the image display areas 41. When the puncture probe 22 is moved while the fixing/release button 31c is pressed, the end is fixed to the center of the image display area 41, and an image and a background are moved according to the motion of the puncture probe.

In case a puncture probe for cauterization for cautery by a radio wave and a microwave is used for the puncture probe 22, cautery equipment not shown that drives a high frequency radiation electrode for the puncture probe for cauterization is provided.

Next, the action and operation of this embodiment will be described.

The ultrasonic probe 21 is connected to the ultrasonic transmitter 11 and the ultrasonic receiver 12 of the body 10. The data of multilevel tomographic images generated in the B-mode processor 13a or the color-mode processor 13b is supplied to the three-dimensional image generator 40. The three-dimensional image generator 40 generates the data of a two-dimensional display image in which the end position of the puncture probe 22 is fixed to the specific position in the image display area 41 of the monitor 32 according to the position and the direction of the ultrasonic probe 21 and those of the puncture probe 22 based upon the data of the multilevel tomographic images. The two-dimensional display image is a multiplanar reconstruction (MPR) image or a rendered image. The display output device 14 forms the screen of the monitor 32. In a part of the screen, the image display area 41 of predetermined narrow size is arranged. In the image display area 41, a display image is arranged. The display image enables the stereoscopic observation of an internal organ and a tumor. The output of the ultrasonic receiver 12 is processed to be tomographic image data corresponding to a display mode such as tomographic image data for formal description by the B-mode processor 13a or tomographic image data for describing ultrasonic Doppler blood flow by the color-mode processor 13b and is input to the three-dimensional image generator 40 and then to the display output device 14. That is, the body 10 of the ultrasonic diagnostic equipment can display tomographic image data as a two-dimensional tomographic image.

In the body 10 of the ultrasonic diagnostic equipment, system control is made by CPU 15, temporally continuous plural tomographic image data are stored in the cinememory 19, these are continuously reproduced, and a dynamic image is displayed on the monitor 32. Besides, individual tomographic image data is recorded in the image memory, is displayed on the monitor 32, and reproduction and reference are enabled at any time. Further, diagnostic image data acquired in another medical department such as an ultrasonic diagnostic image, a CT diagnostic image and an MRI diagnostic image is stored in the image memory via an in-hospital network and can be displayed on the monitor 32.

Figure 2:
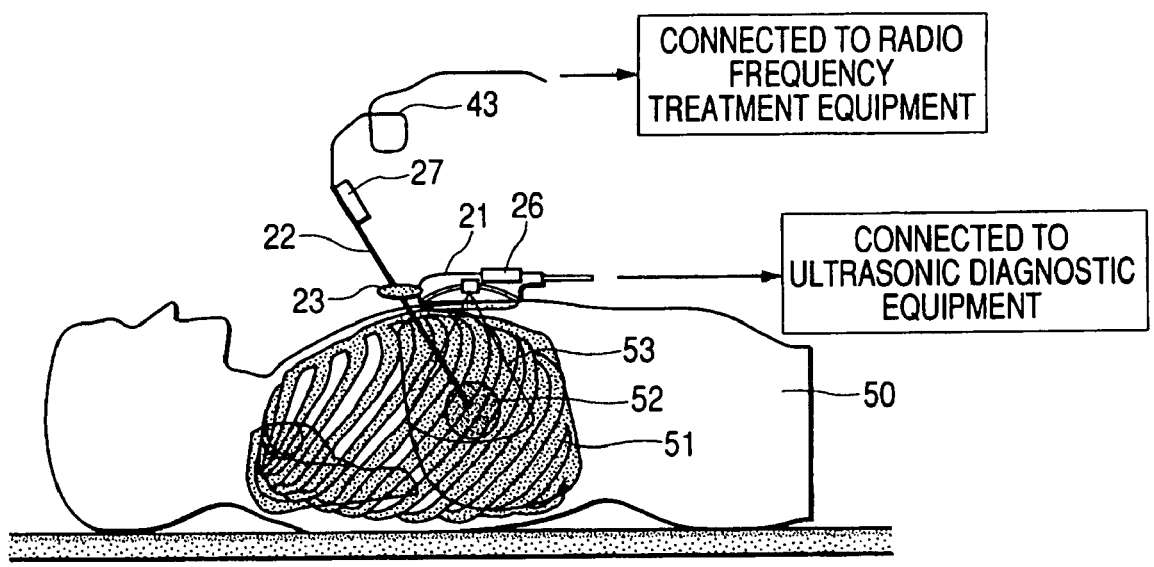
FIG. 2 is a schematic drawing showing the 1-1 embodiment of the invention.

As shown in FIG. 2, the ultrasonic probe 21 is equipped with the position sensor A 26 and the 6-axis coordinates of the ultrasonic probe 21 in coordinate space, that is, the three-axis coordinates of the x-, y- and z-axes and angles of rotation (directions) of the x-, y- and z-axes are detected by a position sensor receiver 25. For example, suppose that the coordinate space having a position in which the position sensor receiver 25 is installed as an origin is first coordinate space. The detected data is input to CPU 15 as probe directional data and three-dimensional data as sliced tomographic images acquired by the ultrasonic probe 21 is provided. In the meantime, the six-axis coordinates in the first coordinate space of the puncture probe 22 are detected by the position sensor B 27 installed on the puncture probe 22 and similarly, the position and the inserted direction of the puncture probe 22 are provided to CPU 15.

The position sensor A 26 and the position sensor B 27 may be also detachable to use them for an ultrasonic probe of general ultrasonic diagnostic equipment or a puncture probe for puncture remedy which are respectively not equivalent to this embodiment.

In the database 16, various settings are stored. For example, the database stores list data including the specifications (the kinds and inserted angles of applicable puncture probes) of the puncture adaptor 23 installed on the ultrasonic probe 21 and the specifications (the diameter and the length) of the inserted puncture probe 22 and further, control system data such as the configuration instructed via a function key of the console panel 31a (a three-dimensional image, a two-dimensional tomographic image, a Doppler color tomographic image and the multi-display combination with another modal image such as a CT image and an MRI image) of a display image on the monitor 32.

The three-dimensional image generator 40 reconstructs plural tomographic images caught by the ultrasonic probe 21 on first spatial coordinates based upon three-dimensional data (multilevel tomographic image data) in a slice direction by the position sensor A 26 and constructs a false three-dimensional image (two-dimensional image) for providing a stereoscopic view. Further, the three-dimensional image generator 40 requests CPU 15 to operate the contour and the position of the puncture probe 22 based upon positional data by the position sensor B 27 and the specification data of the target puncture probe in the database 16 and similarly constructs these on the first spatial coordinates as a puncture probe display image. A part at the end of the probe in the puncture probe display image is displayed at higher intensity or with a falsely thicker diameter than the body of the probe to facilitate identification.

In case the puncture adaptor 23 is installed on the ultrasonic probe 21 and the puncture probe 22 is inserted under the guidance of this, the puncture probe 22 is generally guided in a field of view (on a slice) of a tomographic image of the ultrasonic probe 21 and therefore, an echoic image of the puncture probe 22 can be observed in the tomographic image on one screen. Therefore, in puncture utilizing the puncture adaptor, positional data from the respective position sensors 26, 27 are replaced with the two-dimensional space (a tomographic image) in a scanning direction of the ultrasonic probe 21 on the first spatial coordinates, the image construction device 18 constructs a so-called one-screen tomographic image, and a calculated puncture probe display image is written onto the tomographic image in a state also including the highlighting of the part at the end of the probe. On the monitor 32, the echoic image of the puncture probe 22 is included in the original tomographic image acquired by the ultrasonic probe 21 though the reflective intensity is low and the puncture probe display image is displayed together with a real image of the puncture probe 22. The puncture probe display image in this embodiment is written based upon data detected by the position sensor B 27 and is different from the display of an intrinsic insertion set directional traverse according to the preset specification (insertion angle) of the puncture adaptor while the conventional type puncture adaptor is used.

The three-dimensional image generator 40 executes processing for altering a bird's-eye position of an image including the reconstructed puncture probe display image according to an instruction set via the input device 31a such as a trackball of the input means 31 of rotational quantity and the quantity of displacement related to the alteration of a view point and a direction of a line of sight for rendering on the first spatial coordinates.

The image construction device 18 stores the position coordinate data of the end of the puncture probe 22 at that time according to an instruction via a function key, "probe end marking" of the console panel 31a, writes data for displaying "a probe end mark" in the form of a line on the stored position coordinates of the probe end to the image data of a three-dimensional ultrasonographic image and a tomographic image, and displays "the probe end mark" on the monitor 32 together with the ultrasonotomographic image. The storage of the position coordinate data is also maintained after the puncture probe 22 is extracted and is deleted according to an instruction to delete probe end data.

The three-dimensional image generator 40 sets second coordinate space having the above-mentioned stored position coordinate data of the probe end as an origin to be a criterion according to an instruction via a function key, "probe end mark relative display" of the console panel 31a after the above-mentioned "probe end marking". The origin of the second coordinate space is located in the center of the image display area 41 of a rendered image. The input of the instruction via the function key, "probe end mark relative display" corresponds to operation for turning on the fixing/release button 31*c* provided for a single purpose. While the fixing/release button 31*c* is pressed, the end position of the puncture probe 22 is fixed to a specific position on the screen of the monitor 32, typically to the center of the area (the image display area) 41 allocated beforehand to display an image. When the puncture probe 22 is moved while the fixing/release button 31*c* is pressed, the end is fixed to the center of the image display area 41, and an image and the background are moved according to the motion of the puncture probe.

A tomographic image caught by the ultrasonic probe 21 is operated and converted to a relative position to the position coordinate data of the probe end based upon three-dimensional data in the slice direction by the position sensor A 26 on the first coordinate space detected by the position sensor receiver 25, is reconstructed on the second spatial coordinates and a tomographic image is constructed. The origin to be a criterion corresponds to the specific position (for example, a center position) in the image display area 41. Further, the contour and the position of the puncture probe 22 are similarly operated and converted to a relative position to the position coordinate data of the probe end in CPU 15 based upon positional data by the position sensor B 27 and the specification data of the target puncture probe in the database 16 and are also constructed on the second spatial coordinates as a puncture probe display image. The highlighting of the probe end part in the puncture probe display image is similar to the above-mentioned.

A position in the displayed image is designated as a position of the origin to be a criterion by operating the trackball of the input device 31*b* according to an instruction via a function key, "origin setting" of the console panel 31*a* in place of the above-mentioned stored position coordinate data of the probe end and second coordinate space is set. The display position of an ultrasonotomographic image and a puncture probe image can be freely changed by designating the position of the origin to be a criterion.

The three-dimensional image generator 40 requests CPU 15 to operate the contour and the position of the puncture probe 22 based upon positional data by the position sensor B 27 on the first coordinate space detected by the position sensor receiver 25 every moment and the specification data of the target puncture probe in the database 16 according to an instruction via a function key, "probe end relative display" of the console panel 31*a* and sets third coordinate space having the momentary position coordinate data of the probe end as an origin to be a criterion. The origin to be a criterion corresponds to the specific position (for example, a center position) of the image display area 41. Further, a tomographic image caught by the ultrasonic probe 21 is operated and converted to a relative position to the above-mentioned momentary position coordinate data of the probe end based upon three-dimensional data in the slice direction by the position sensor A 26 detected by the position sensor receiver 25, is reconstructed on the third spatial coordinates and a tomographic image is constructed. The contour and the position of the puncture probe 22 the probe end of which is located at the origin to be a criterion are also constructed on the third spatial coordinates as a puncture probe display image and it need scarcely be said that this is the data of a fixed puncture probe display image. A puncture probe set image and a tomographic image respectively constructed on the third spatial coordinates are displayed on the monitor 32.

Next, the details of the embodiment of the invention will be described referring to schematic drawings showing the operation of the ultrasonic probe 21, the insertion of the puncture probe 22 and examples of display on a screen of the monitor 32.

FIG. 2 is a schematic drawing showing the 1-1 embodiment by the ultrasonic diagnostic equipment according to the invention. A target part 51 of a patient 50 shown in FIG. 2 is a liver and an example using a puncture probe provided with an electrode for a radio wave in case cautery by a radio wave is applied to hepatic cancer to be treated 52 at the end will be described below.

FIGS. 3A to 3F show examples of tomographic images displayed on the monitor 32 in this embodiment and showing situations in which the puncture probe is operated.

As shown in FIG. 2, the patient 50 is laid in standard therapeutic posture in the case of treatment by the puncture probe 22 and the ultrasonic probe 21 provided with the position sensor A 26 is set closely on the surface of the body over the therapeutic object 52 (the hepatic cancer). The 1-1 embodiment adopts a method of catching the whole inserted puncture probe 22 in a ultrasonotomographic image and the puncture adaptor 23 for guiding the puncture probe 22 in a field of view of a tomographic image (a slice) 53 is attached to the ultrasonic probe 21.

The puncture probe 22 guided by the puncture adaptor 23 and inserted into the therapeutic object is provided with the position sensor B 27 at the base and is provided with lead wire 43 connected to the electrode for a radio wave at the end for radio wave cautery.

The best tomographic image of the therapeutic object 52 can be acquired, operating the ultrasonic probe 21 and observing the tomographic image displayed on the monitor 32 and the ultrasonic probe 21 is held in a position in which the insertion path of the puncture probe 22 can be secured.

Figure 3A:
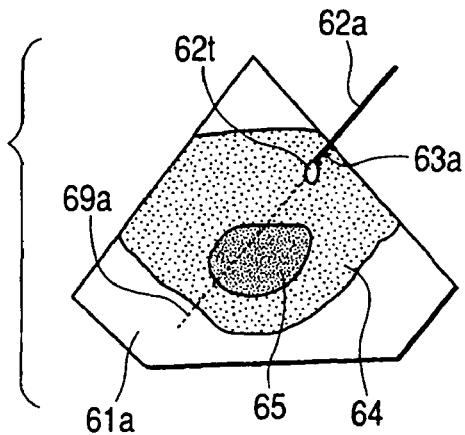
FIGS. 3A to 3F show examples of tomographic images displayed in the 1-1 embodiment in a situation in which a puncture probe is operated.
Figure 3B:
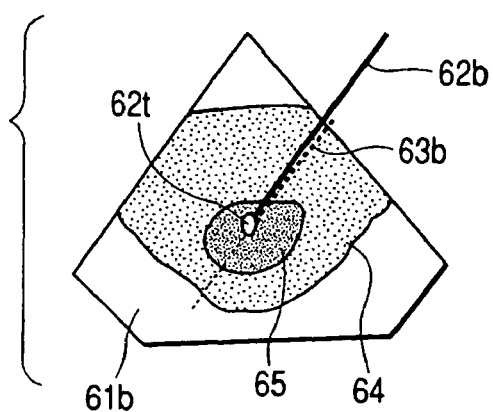

In this embodiment, in case display on the monitor 32 is set to the display of a two-dimensional tomographic image, a two-dimensional tomographic image shown in FIG. 3A is displayed immediately after the puncture probe 22 is inserted to the body, utilizing a puncture guidance hole of the puncture adaptor 23 attached to the held ultrasonic probe 21, and afterward, when the end of the puncture probe 22 reaches the tumor, an ultrasonotomographic image shown in FIG. 3B can be observed.

In FIG. 3A immediately after insertion, a tomographic image 61*a* by the ultrasonic probe 21 provided with the position sensor A 26 is shown and an image of the tumor 65 is shown inside an image of the target internal organ 64. An image 63*a* of the puncture probe 22 immediately after insertion may be displayed by a weak reflected signal.

In the meantime, data from the puncture probe 22 provided with the position sensor B 27 received by the position sensor receiver 25 is input to CPU 15 of the body 10 of the ultrasonic diagnostic equipment, and the position, the inserted direction and the end position of the puncture probe are calculated based upon the data of the puncture probe 22 stored in the database 16. The result of the calculation is written to the first spatial coordinates together with the delineated tomographic image 61*a*, a calculated puncture probe display image 62*a* shown in FIG. 3A is overwritten by displaying a two-dimensional tomographic image in a position sliced by the ultrasonic probe 21, and further, a highlighted probe end mark 62*t* and a puncture probe insertion estimated path 69*a* acquired by extending the puncture probe display image are also displayed at the end of the probe. The probe end mark 62*t* and the puncture probe insertion estimated path 69*a* are generated by the image construction device 18.

The image 63a of the probe displayed by a weak reflected signal may not be displayed in the tomographic image 61a depending upon a situation of the signal, however, the calculated puncture probe display image 62a and the probe end mark 62t are displayed independent of a method of delineating the tomographic image if only the operation of the sensor is normal.

Figure 3C:
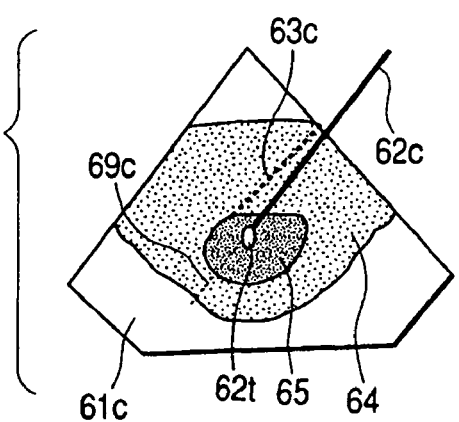

Further, when the insertion of the puncture probe 22 is continued, the observation of the tomographic image 61 displayed on the monitor 32 is continued, the puncture probe display image 62b is extended as shown in FIG. 3B and the probe end mark 62t reaches the vicinity of the center of the tumor image 65 inside the internal organ image 64, the insertion of the puncture probe 22 is stopped. A case that the image of the probe 63c displayed though it is unstable, the puncture probe display image 62c and the puncture probe insertion estimated path 69c are displayed in remarkably apart positions as shown in FIG. 3C proves a case that the puncture probe 22 is curved because of a boundary of tissue and resistance by running and the insertion is not directed in a supposed direction and the insertion is made again.

Figure 3D:
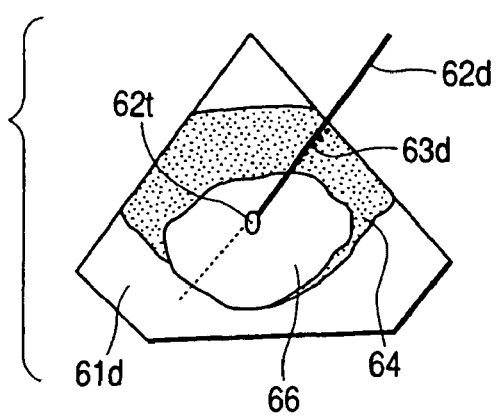

As the end of the puncture probe can be located on the therapeutic object as described above, the part is next treated. For example, in radio wave cautery, cauterization treatment equipment not shown is connected to the electrode for a radio wave of the puncture probe for cauterization via the lead wire 43 and cautery is made by operating the output of the cauterization treatment equipment. Corresponding to the proceedings of cautery, as shown in FIG. 3D, the spread of a whitish high echo area 66 generated by the denaturation of tissue in a cauterized part and foaming is displayed in the circumference of the end 62t of the puncture probe display image 62d inside the image of the internal organ 64 displayed in the tomographic image 61d. The proceedings of treatment on that day can be managed, observing the high echo area 66 and considering the set position of the puncture probe 22, a range of a treatment plan and a situation of the patient. The image of the probe 63d delineating by a reflected signal of ultrasonic cannot be observed because of the high echo area 66, however, as the puncture probe display image 62d and the probe end mark 62t in this embodiment are clearly displayed, there is effect that the management of the treatment is facilitated.

Next, a transformed example of the method of displaying the puncture probe display image 62a and the probe end mark 62t will be described.

Figure 3E:
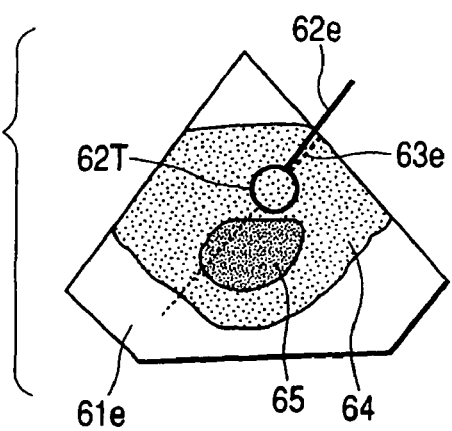
Figure 3F:
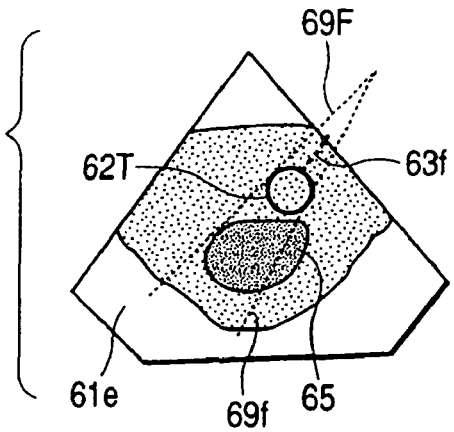

As the position sensor B 27 of the puncture probe 22 is arranged at the base as shown in FIG. 2, the end of the real probe may be off an estimated position because of distortion and flexure in insertion. This displacement may be off not only the tomographic image but a sliced layer. The image construction device 18 displays the end of the probe as the puncture probe end mark in an area 62T set to the magnitude of estimated displacement in consideration of such displacement as shown in FIG. 3E. Further, the image construction device 18 generates puncture estimated path images 69F, 69f directed in directions of estimated displacement in consideration of displacement between the puncture probe display image and the calculated real position of the puncture probe as shown in FIG. 3F and displays a range in which the puncture probe 22 is inserted. That is, the magnitude of the displayed probe end mark 62t is determined depending upon the magnitude of the displacement between the estimated insertion directions of the puncture probe and may be also the area 62T.

According to this embodiment, the contour and the position of the inserted puncture probe are operated based upon positional data including directional data by the position sensors provided to the ultrasonic probe and the puncture probe. As the result of the operation is overwritten to a tomographic image by the ultrasonic probe as a puncture probe display image, it is more clearly displayed than a real ultrasonotomographic image of the puncture probe in which only a weak reflected signal is acquired and stable display in the tomographic image is difficult. Therefore, a position in which the puncture probe is inserted can be definitely recognized and the puncture probe can be safely and easily inserted.

In case only a two-dimensional tomographic image is displayed in this embodiment, it is one method for the definite display of the position of the puncture probe which is the object of the invention to limit the above-mentioned operation to the operation of two-dimensional data on an ultrasonotomographic layer (a slice) and to accelerate operation.

1-2 Embodiment

Figure 4:
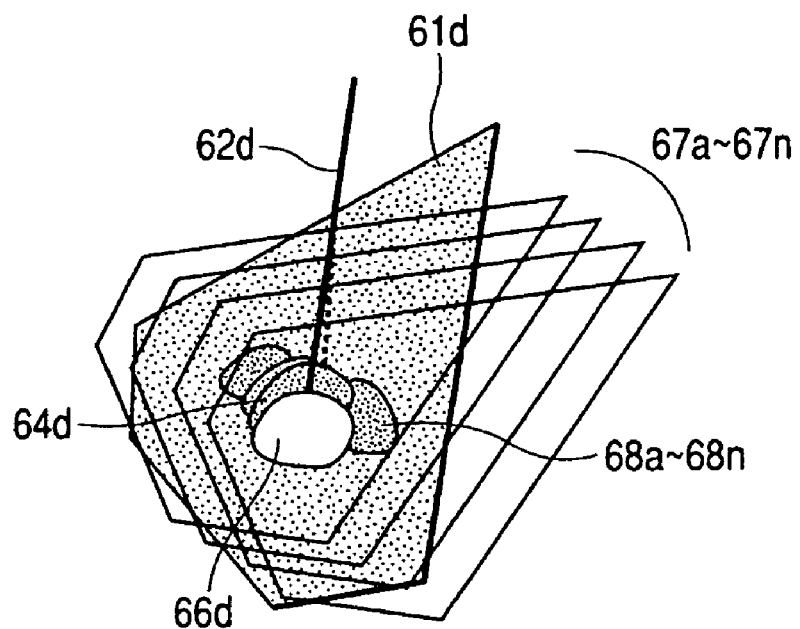
FIG. 4 is a schematic drawing showing the retrieval and the display of a therapeutic target part in a 1-2 embodiment.

FIG. 4 is a schematic drawing showing another example related to the retrieval and the display of a therapeutic target part in the ultrasonic diagnostic equipment according to the invention.

In this embodiment, a three-dimensional image generation process by a three-dimensional image generator 40 is executed beforehand before insertion. In first coordinate space having the position of a position sensor receiver 25 as a criterion, the stereoscopic display 67a to 67n of a target part is made on a monitor 32 as shown in FIG. 4 and is temporarily stored in an image memory 17. Next, in the retrieval of the held position of an ultrasonic probe 21 for the insertion of a puncture probe 22, a tomographic image (a slice) 61d is overlapped with the position of the probe by a position sensor A 26 in the first coordinate space. The stereoscopic display is acquired by acquiring three-dimensional image data by the technique of the conventional type so-called three-dimensional ultrasonographic diagnostic equipment, referring to a predetermined common criterion and writing on first spatial coordinates again. A display mode of a tomographic image may be any of a B mode, a color Doppler mode, a pulse Doppler mode, a continuous wave Doppler mode, a contrast mode and elastic imaging respectively generally applied in ultrasonic diagnostic equipment, and a display mode corresponding to the disposition and the property of a therapeutic object is selected.

In case the tomographic image 61d for observing the insertion of the puncture probe 22 in a direction different from a slice direction of the stereoscopic tomographic images 67a to 67n is set, the different sectional image 64d of therapeutic object images 68a to 68n can be observed. Particularly, after cautery is started, a range of treatment is checked by contrasting the spread of a cauterized whitish high echo area 66d with the original therapeutic object images 68a to 68n and cautery such as the output of cauterization and cauterization time is controlled.

In this embodiment, as a therapeutic object is stereoscopically caught, the inserted position of the puncture probe is set to a detailed position of the therapeutic object and the puncture probe can be inserted. Besides, as a range of treatment can be stereoscopically grasped and the efficiency and the effect of treatment are enhanced, the correspondence is facilitated.

1-3 Embodiment

A 1-3 embodiment in the ultrasonic diagnostic equipment according to the invention will be described, referring to FIG.

5 which is a schematic drawing showing the insertion of a puncture probe in this embodiment and FIGS. 6A to 6F showing its display images below.

In this embodiment, as in the method shown in FIG. 2 and FIGS. 3A to 3F in the 1-1 or 1-2 embodiment, the puncture probe 22 is first inserted via a puncture adaptor 23 installed on an ultrasonic probe 21. Further, as shown in FIGS. 3A to 3F, the puncture probe is inserted until the end of the puncture probe 22 reaches a tumor of a therapeutic object and a probe end mark 62t reaches the vicinity of the center of a tumor image 65 inside an internal organ image 64.

When the probe end mark 62t approaches the vicinity of the center of the tumor image 65, a function key, "probe end marking" of a console panel 31b is set and a probe end position in first coordinate space as the center position data of the target tumor is stored in an image memory 18 together with tomographic image data. In case the tomographic image is recorded as a dynamic image, function keys, "cine recording" and "probe end marking" of the console panel 31b are set, and the dynamic data of an ultrasonotomographic image and center position data are stored in a cinememory 19.

Then, function keys, "therapeutic object redisplay" or "cine image regeneration" and "probe end mark relative display (probe end position fixed display)" of the console panel 31b are set. The setting of "probe end mark relative display (probe end position fixed display)" is input by turning on a fixing/release button 31c. While the fixing/release button 31c is pressed, the end of the puncture probe 22 is fixed to a specific position on the screen of a monitor 32, typically the center of an image display area 41. When the puncture probe 22 is moved while the fixing/release button 31c is pressed, the end is fixed to the center of the image display area 41, and an image and the background are moved according to the motion of the puncture probe. By the setting, a tomographic image in which the position of a target tumor is set or a tomographic cinema is converted in second coordinate space having the probe end position as an origin to be a criterion and a tomographic image having the probe end position in the center of the display area 41 is displayed on the monitor 32 like a tomographic image 72 in a schematic drawing shown in FIG. 6A.

Figure 5:
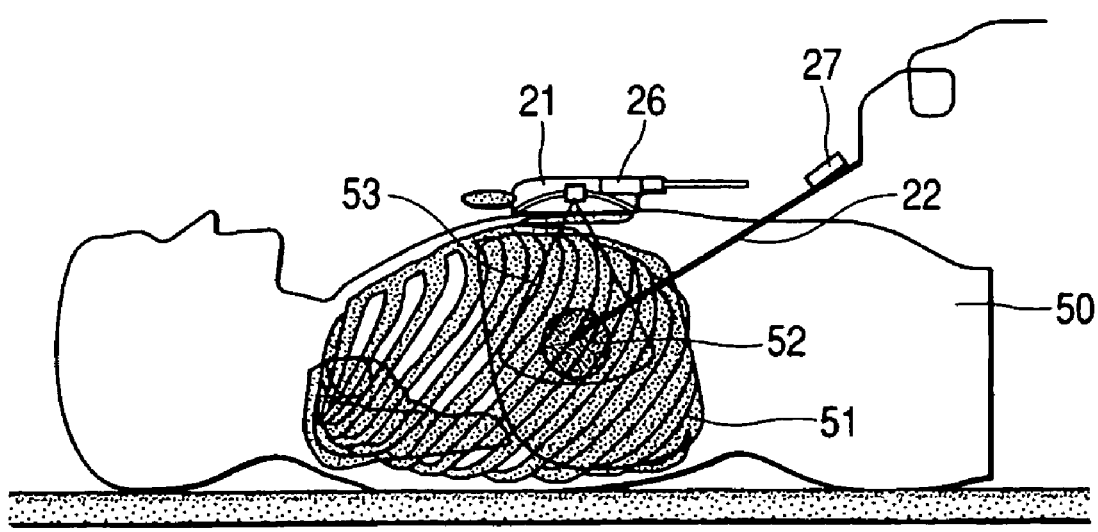
FIG. 5 is a schematic drawing showing the insertion of a puncture probe in 1-3 and 1-4 embodiments.
Figure 6A:
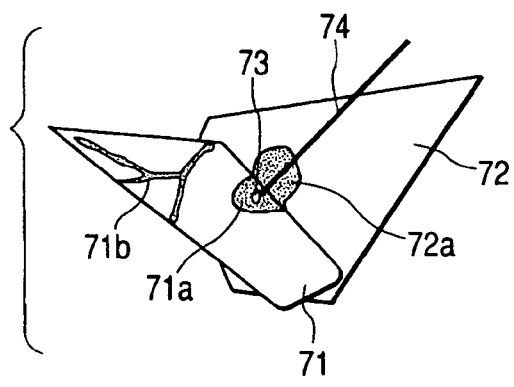
FIGS. 6A to 6F are schematic drawings showing the retrieval and the display of a therapeutic target part in the 1-3 and 1-4 embodiments.

Next, as shown in FIG. 5, the ultrasonic probe 21 is independently placed on the surface of the body of a patient, a target internal organ or tumor is caught in a field of view of an ultrasonotomographic image (a slice) and a target part is observed at various angles. That is, as shown in FIG. 6A, after the above-mentioned puncture adaptor is installed and the tumor 72a in the acquired tomographic image 72 is observed, the puncture adaptor is detached from the probe (the coupling of the puncture probe 22 and the ultrasonic probe 21 is released) and a tumor 71a in a tomographic image 71 from a different direction is observed. The observation of the tomographic image 71 is displayed in the same coordinate space by a position sensor A 26 and the tomographic image can be observed in a sense of three dimensions. Further, for example, a blood vessel 71b around the tumor and the positional relation of the tumor 71a can be also checked with the tomographic image.

Tomographic image data 71 scanned via the ultrasonic probe 21 and immediately generated by a B mode processor 13a is displayed on the monitor 32 together with the tomographic image 72 stored in the image memory 18 by setting "probe end marking" and a tomographic image (not shown) stored in the cinememory 19 as shown in FIG. 6A. The tumor can be observed from various directions at real time as the tomographic image 71 by changing the position of the ultrasonic probe 21. When the probe end position is not suitable, the inserted position of the probe is adjusted. During adjustment, a probe end mark 73 is fixed and the motion of the probe end can be also checked with a live image of the tomographic image 71. The probe end mark 73 and a puncture probe display image 74 are updated in the latest positions after adjustment by setting "probe end mark relative display" and are displayed again.

1-4 Embodiment

Referring to FIGS. 5 and 6A to 6F, a 1-4 embodiment will be described below.

In this embodiment, first an ultrasonic probe 21 is independently placed on the surface of the body of a patient as shown in FIG. 5 without utilizing a puncture adaptor, a tumor of a target internal organ, its ambient internal organs and its ambient blood vessels are scanned, an inserted position and a puncture path are observed and determined. A position in which the tumor can be caught in a field of view of an ultrasonotomographic image and a clear tomographic image of a target part is acquired is a therapeutic observation position.

Figure 6B:
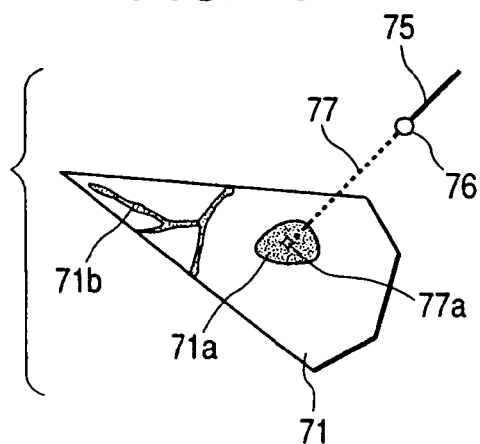

Next, the ultrasonic probe 21 is held in the therapeutic observation position, the end of a puncture probe 22 provided with a position sensor B 27 is located in the vicinity of the surface of the body of a patient 50, and the puncture probe is set in its inserted direction. FIG. 6B is a schematic drawing in which the tomographic image 71 in the therapeutic observation position is displayed in three-dimensional coordinate space on a monitor 32. A puncture probe display image corresponding to the puncture probe 22 directed in the inserted direction or a linear mark 75 and a probe end mark 76 corresponding to the puncture probe 22 and generated in a reconstruction device 18 according to the position, the direction and the size of the puncture probe 22 are displayed. The puncture probe display image 75 and the probe end mark 76 are generated by the image reconstruction device 18. Further, a linear puncture probe insertion estimated path (an insertion estimated path) 77 to the tomographic image 71 in the therapeutic observation position generated in the reconstruction device 18 according to the position and the direction of the puncture probe 22 is displayed. The insertion estimated path 77 is displayed in a mode different from the linear mark 75. The linear mark 75 corresponding to the puncture probe 22 is displayed by a full line and the linear mark 77 corresponding to the insertion estimated path is displayed by a dotted line or a broken line. A cross-point 77a of the tomographic image 71 and the insertion estimated path 77 is also displayed. The data of the image 71 in which the linear mark 75, the linear mark 77 and the probe end mark 76 are synthesized is stored in a storage 17.

When the puncture probe 22 is moved, the puncture probe display image 75, the probe end mark 76 and the puncture probe insertion estimated path 77 are moved together on the monitor 32 and these positions are updated.

For a method of displaying on the monitor 32, in case display is made with the position of the probe end as a criterion, a display mode that the tomographic image 71 is relatively moved without moving the display of the puncture probe is also possible. The puncture probe is inserted, observing the tomographic image 71, the puncture probe display image 75, the probe end mark 76 and the puncture probe insertion estimated path 77 respectively displayed as described above and checking the position of the puncture probe 22.

When the puncture probe reaches a target insertion position, an electrode for a radio wave of the puncture probe 22 is connected to cautery equipment and cautery is executed.

When the treatment is started, the generation of a high echo area by the denaturation of tissue and foaming can be observed in the vicinity of the end of the puncture probe in the tomographic image 71. To observe and verify the proceedings of the treatment, the position and the direction of the ultrasonic probe 21 are variously operated and a desired tomographic image 71 is displayed on the monitor 32. Particularly, an image of a part at the back of the high echo area is called an echo shadow because of a characteristic of an ultrasonic signal, observation from its direction is difficult, and the image is required to be observed in a state in which the position of the ultrasonic probe 21 is displaced in a different direction.

Figure 6C:
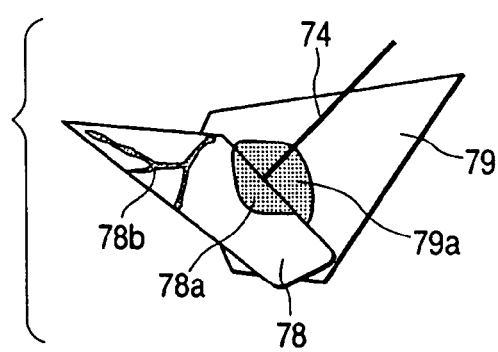

When the fixing/release button 31c is turned on, the probe end position is fixed to the center of the image display area 41 of the monitor 32 as shown in FIG. 6C. Even if the orientation of the probe 21 is changed, the image 71 is displayed in a state in which the probe end position is ordinarily located in the center of the image display area 41. That is, the displayed position and orientation of the tomographic image 71 are changed according to the change of the orientation and the position of the probe 21 in a state in which the probe end position is fixed to the center of the image display area 41. Even if the puncture probe 22 is moved, a displayed image is updated according to the motion of the puncture probe 22 so that the probe end is located in the center of the image display area 41.

A tomographic image and the position of the puncture probe are caught in three-dimension coordinate space by the ultrasonic probe 21 provided with a position sensor A 26 and the puncture probe 22 provided with the position sensor B 27, therapeutic objects 78a, 79a can be observed from various positions and directions during an operation independent of the inserted direction of the puncture probe, and the position and the direction 74 of the puncture probe can be also recognized.

Figure 6D:
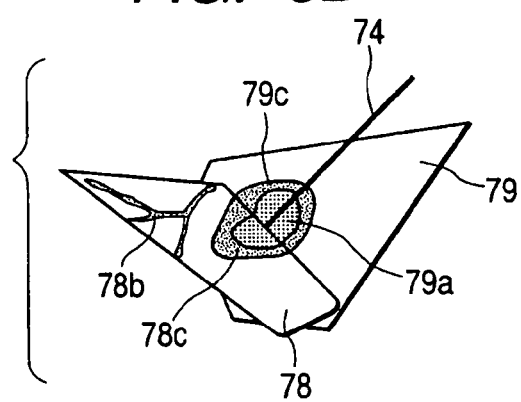

When predetermined energy is injected, cautery is finished. Afterward, the position and the direction of the ultrasonic probe 21 are variously operated, the cauterized images 78c, 79c after treatment of tomographic images 78, 79 shown in FIG. 6D are displayed on the monitor 32, and a situation of cauterization is observed. An image 78b of ambient blood vessels is observed and the effect of treatment can be also checked.

Figure 6E:
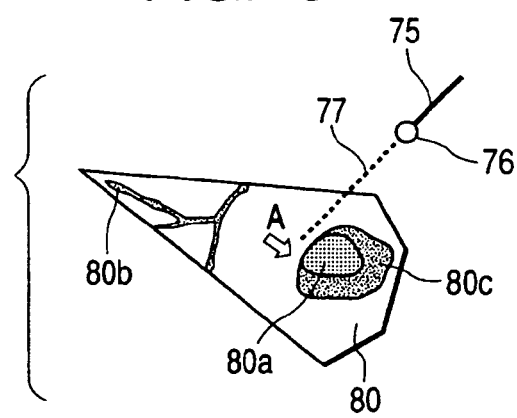
Figure 6F:
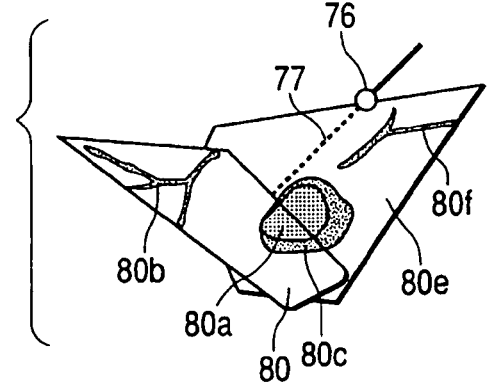

Next, referring to FIGS. 6E and 6F, a case of cauterization executed twice or subsequently in the 1-4 embodiment will be described. After display shown in FIG. 6D, the fixing of the probe end display position is released by turning off the fixing/release button 31c. FIG. 6E shows the similar display to that shown in FIG. 6B and shows an example in which an image of a tumor 80a in a target part is observed in a tomographic image 80 in puncture cautery executed twice or subsequently.

In the tomographic image 80, the image of the tumor 80a and a former, for example, a first cauterized area 80c are observed and in case the cauterization of an area (the probe is located in a pointed part of a fan-shaped image) over the tumor 80a is judged insufficient in the tomographic image 80 by the observation, second cauterization in which the position of a part shown by an arrow A is set to the probe end position is planned to apply additional cauterization to the part shown by the arrow A.

In the additional cauterization, the ultrasonic probe 21 is operated and the puncture probe 22 is set in a state in which the tomographic image 80 including the image of tumor 80a and the image of the last cauterization 80c is displayed. As shown in FIG. 6E, the puncture probe display image 75 and the puncture probe insertion estimated path 77 are displayed based upon the data of the position sensor B 27. Next, the position and the direction of the puncture probe 22 are adjusted so that the puncture probe insertion estimated path 77, the probe end mark 76 and the puncture probe display image 75 are directed to the direction shown by the arrow A planned in the second cauterization and the position and the direction of puncture are determined. Next, as shown in FIG. 6F as in FIG. 6A, the probe 21 is moved in a state in which the tomographic image 80 is recorded and displayed and an ultrasonotomographic layer 80e is also displayed on the monitor 32. It is verified that no blood vessel 80f exists on a puncture probe inserted path including the puncture probe insertion estimated path 77, observing the previous tomographic image 80 recorded and displayed and the tomographic image 80e displayed at real time, and the puncture probe 22 is inserted so that the probe end mark 76 of the puncture probe 22 reaches the vicinity of a planned arrow A. After the insertion, the cautery equipment is connected and treatment is made. After the treatment, as described above, a cauterized range is observed again as in FIG. 6D and the treatment is finished.

1-5 Embodiment

FIGS. 7, 8, 9 and 10 are schematic drawings showing an embodiment of monitor display by the ultrasonic diagnostic equipment according to the invention. In this embodiment, the last tomographic image acquired before cautery or in the last cautery and a real-time tomographic image showing an inserted puncture probe during cautery are simultaneously displayed on two screens in various display modes of a monitor.

Figure 7:
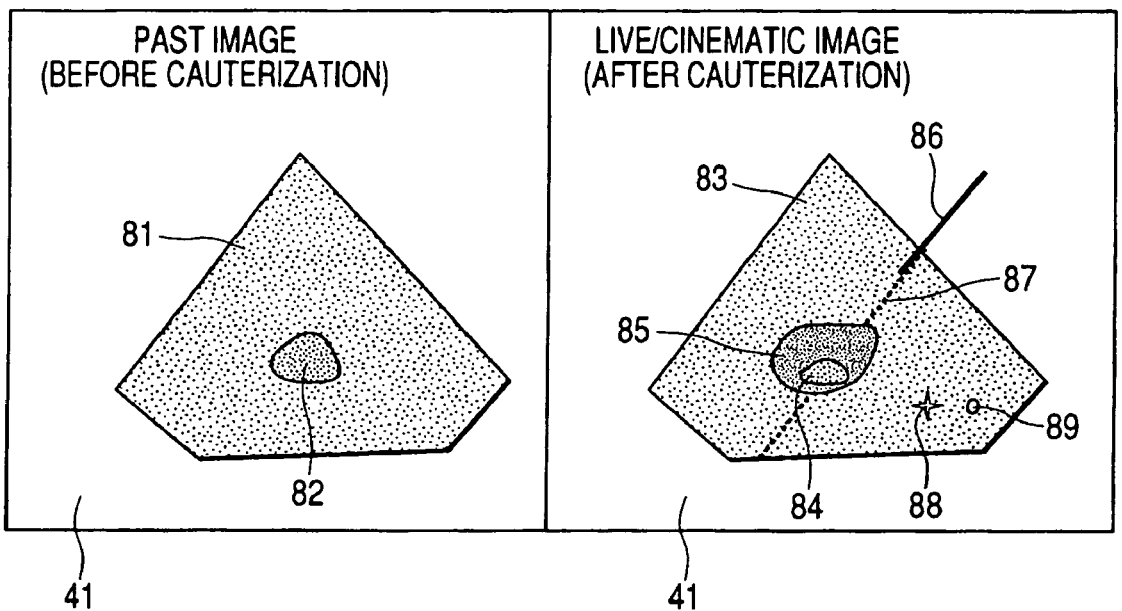
FIG. 7 is a schematic drawing showing a first display example displayed on a monitor in a 1-5 embodiment.

In a first display example shown in FIG. 7, a tomographic image 81 formerly acquired and recorded is displayed including an image of a tumor 82 verified as a therapeutic object on the left side for example of the monitor 32. On the right side, a real-time tomographic image 83 observed by an ultrasonic probe 21 is displayed including an image of the tumor 84 treated by the puncture probe 22.

Next, when the puncture probe 22 provided with a position sensor B 27 is set in the vicinity of the surface of the body over a target internal organ in an inserted direction, signals from the position sensor B 27 and a position sensor A 26 provided to the ultrasonic probe 21 are received by a position sensor receiver 25 and respective positional data are input to CPU 15 in the body 10 of the ultrasonic diagnostic equipment. In CPU 15, the data of spatial coordinates showing relation between a slice position of a tomographic image observed by the ultrasonic probe 21 and an insertion path estimated position of the puncture probe 22 or an inserted position is immediately operated.

An image of the insertion path estimated position 87 or a puncture probe display image 86 is synthesized with the tomographic image 83 displayed at real time based upon the calculated data by an image construction device 18, is input to the monitor 32, and the tomographic image 83 including the puncture probe display image 86 is displayed on the right screen of the monitor 32. The tomographic image 83 shown on the right in FIG. 7 is a display example in case the puncture probe 22 is inserted in the same direction as scanned slice width of the ultrasonic probe 21. Besides, in case the puncture probe 22 is inserted at an angle not parallel with a scanned slice, a positional mark for identifying the following position is overwritten in a position in which the insertion is estimated or in an inserted position as shown as an example 88 of the estimated position and an example 89 of the inserted position on the right downside of the tomographic image 83 shown in FIG. 7 and is displayed on the monitor 32.

When an electrode for a radio wave of the inserted puncture probe 22 is connected to cautery equipment and cautery is executed, an area 85 to which cautery is applied is displayed on the monitor 32 and the proceedings of the treatment can be grasped.

Figure 8:
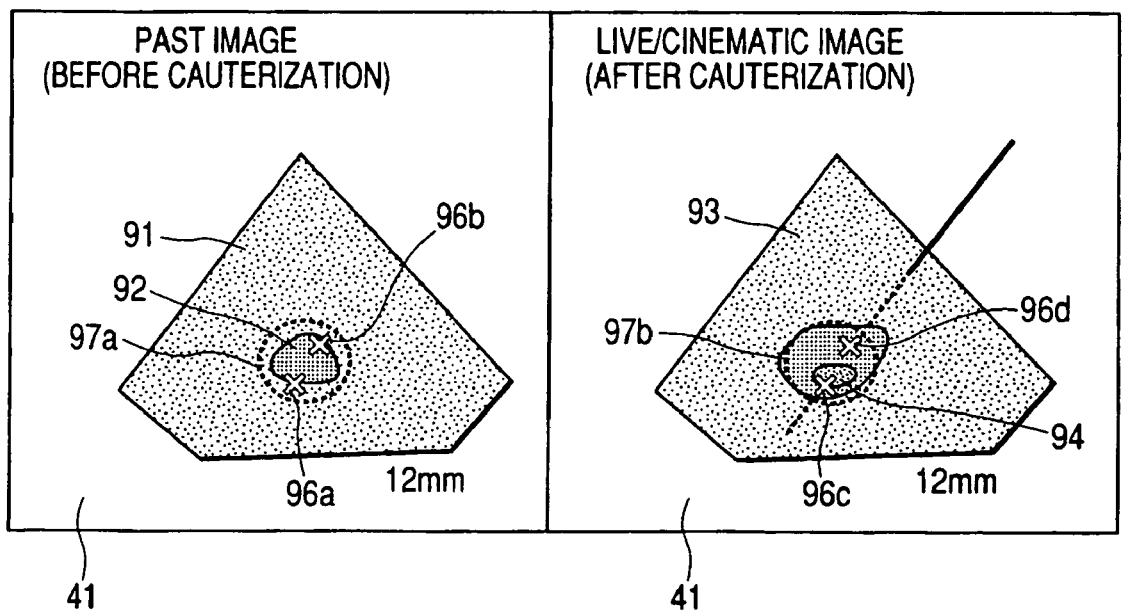
FIG. 8 is a schematic drawing showing a second display example displayed on the monitor in the 1-5 embodiment.

FIG. 8 shows a second display example in the above-mentioned embodiment. A tomographic image 91 formerly acquired and recorded is displayed on the left for example of the monitor 32 together with an image of a tumor 92 verified as a therapeutic object and on the right, a real-time tomographic image 93 observed by the ultrasonic probe 21 is displayed together with an image of a tumor 94 to be treated by the puncture probe 22 and an image of a cauterized area 95. Two points 96a, 96b in the former tomographic image 91 displayed on the left side of the monitor 32 for example are designated by a trackball or others which is an input device 31b in the body 10 of the ultrasonic diagnostic equipment, distance between the two points is instructed to be measured, a graphic form such as a circle 97a or an ellipse is instructed to be drawn, and the diameter or the area is instructed to be measured. Their coordinate values are read by these instructions, are overwritten to the data of the real-time tomographic image 93 in related positions and size by the image construction device 18, and their copies 96c, 96d, 97b are displayed on the tomographic image 93. The measurement and the copy of a graphic form are similarly made from the real-time tomographic image 93 into the former tomographic image 91.

Figure 9:
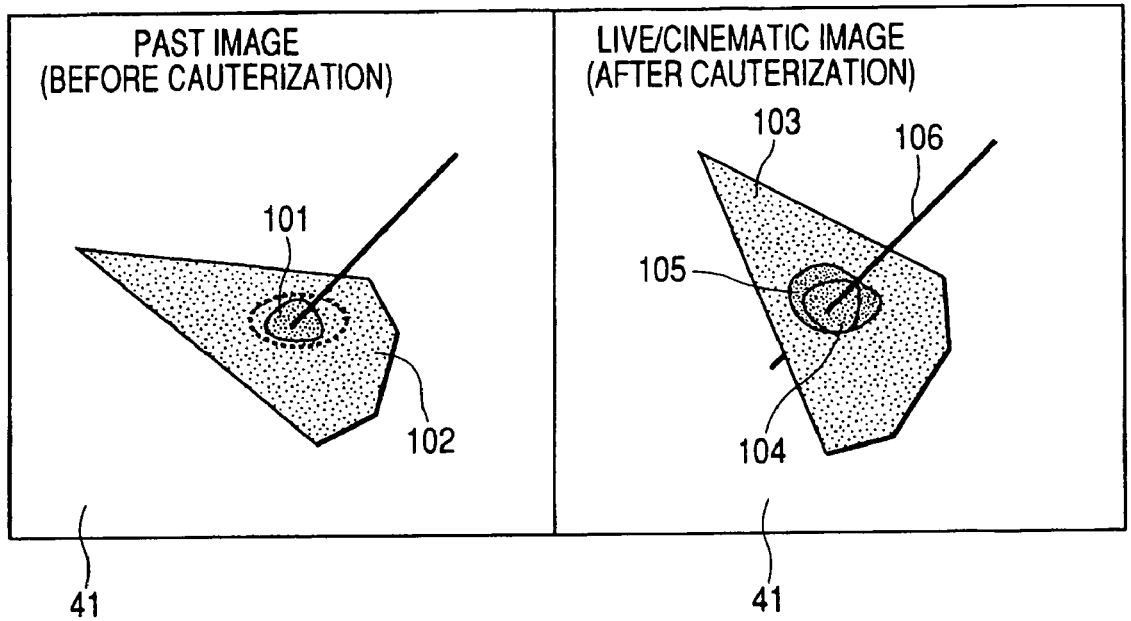
FIG. 9 is a schematic drawing showing a third display example displayed on the monitor in the 1-5 embodiment.

FIG. 9 shows a third display example in the above-mentioned embodiment. On the left of the monitor 32 for example, a formerly acquired and recorded tomographic image 101 including an image of a tumor 102 verified as a therapeutic object is displayed and on the right, a real-time tomographic image 103 including an image of a tumor 104 treated by the puncture probe 22 and a cauterized area image 105 and observed by the ultrasonic probe 21 is displayed, and these tomographic images are three-dimensionally displayed on first spatial coordinates.

In the real-time tomographic image 103 displayed on the right side in this display example on the monitor 32, differently from the first and second display examples, independent of the picked position and direction of the tomographic image (a slice), a display image 106 of the inserted puncture probe is all displayed. The real-time tomographic image 103 including the image of the tumor 104 and the cauterized area image 105 respectively three-dimensionally displayed and the puncture probe display image 106 are observed, and positional relation between the puncture probe 22 and the target tumor 52 and a situation of cautery can be stereoscopically grasped.

Further, a function key, "probe end relative display" of the console panel 31b is set. This setting is detected by the position sensor receiver 25 and tomographic image data in the first coordinate space caught by the ultrasonic probe 21 is reconstructed in the third coordinate space having the coordinate data of the position of the end of the puncture probe 22 as an origin to be a criterion by the operation and conversion of the coordinate data of the position of the probe end in a relative position. A real-time tomographic image and a display image of the inserted puncture probe 22 respectively reconstructed in the third coordinate space are displayed on the monitor 32.

Normally, inside an organism, there is respiratory displacement. Particularly, an image of an internal organ in an abdomen and an image of the puncture probe inserted into it are displayed on the monitor in the form of a periodically largely oscillatory image. As the tomographic image and the puncture probe display image respectively converted on the third spatial coordinates have the end of the probe inserted into the target internal organ as the origin, they can be displayed in a relatively stationary state in which the oscillation is removed.

Figure 10:
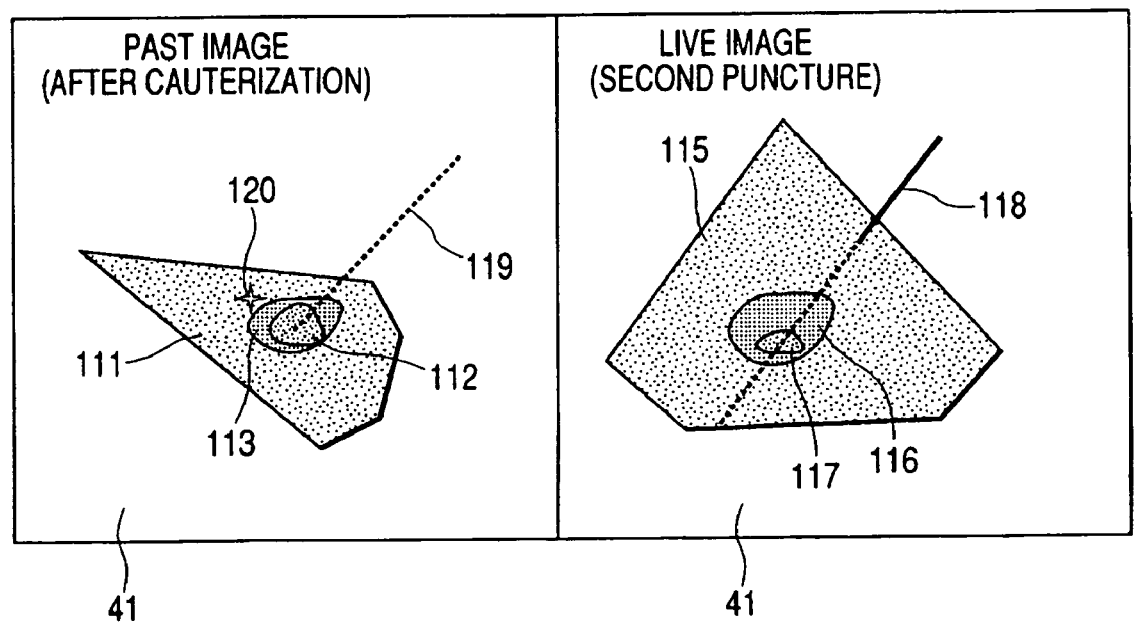
FIG. 10 is a schematic drawing showing a fourth display example displayed on the monitor in the 1-5 embodiment.

FIG. 10 shows a fourth display example in the above-mentioned embodiment. The tomographic images 80, 80f shown in FIG. 6F and described in the 1-4 embodiment are independently displayed on the right of dual screens. That is, on the left of the monitor 32 shown in FIG. 10 for example, a tomographic image 111 including an image of a tumor 112 which is a therapeutic object and a cauterized area image 113 respectively acquired and recorded in the last cautery is three-dimensionally displayed, and on the right, a real-time tomographic image 115 observed by the ultrasonic probe 21 provided with a puncture adaptor and including an image of a tumor 116 to which treatment set in the puncture adaptor by the puncture probe 22 is applied and a puncture probe display image 118 is two-dimensionally displayed.

On the screen on which a past situation is displayed and which is shown in the fourth display example on the left of the monitor 32, the data of the position of the puncture probe is also recorded together with tomographic image data when the last cautery is finished and a puncture probe display image 119 is displayed in a state in which it is shown by a dotted line or an alternate long and short dash line together with the tomographic image 111.

Further, the puncture probe 22 inserted via the puncture adaptor 23 in this cautery is displayed in the tomographic image 111 in the form of a mark 120 for identifying a location for reaching the position on a tomographic layer in the last cautery. The precise insertion and guidance of the puncture probe 22 based upon a treatment plan such as the treatment of the same location as that at the last time or the treatment of a different location are enabled by the mark 120 showing the reached position.

The cautery by the radio frequency puncture probe has been described, however, in percutaneous ethanol injection treatment, if a hollow puncture probe for ethanol injection is used for a puncture probe, the observation and the grasping of a situation of puncture/cautery by the puncture probe which is the object of the invention are similarly enabled.

For an observation image of a former therapeutic part displayed on one of the two screens of the monitor 32, in addition to a three-dimensional ultrasonographic image, an ultrasonotomographic cine (dynamic) image, a CT image or an MRI image of the corresponding patient acquired via an in-hospital network or these three-dimensional image data sets can be similarly referred. In the case of the data of the CT image or the MRI image, alignment is facilitated by providing origin coordinates input means for observing a tomographic image and visually inputting the position of the original to be a criterion of the second spatial coordinates in case a live image of the tomographic image shown in FIG. 9 or 10 is displayed by the side.

1-6 Embodiment

Referring to a schematic drawing shown in FIGS. 11A and 11B, a 1-6 embodiment of the invention will be described below.

A three-dimensional ultrasonographic image by the ultrasonic diagnostic equipment according to the invention is not limited to an image three-dimensionally scanned by manually operating an ultrasonic probe and acquired by reconstructing three-dimensional tomographic image data based upon a two-dimensional tomographic image. A three-dimensional tomographic image by a mechanical three-dimensional ultrasonic probe for three-dimensionally scanning by the mechanical parallel motion or the mechanical rotational motion of the ultrasonic probe or a three-dimensional tomographic image by an electronic three-dimensional ultrasonic probe for electronically scanning three-dimensionally based upon a two-dimensional array probe can be similarly applied for a three-dimensional tomographic image by the ultrasonic diagnostic equipment according to the invention.

Figure 11A:
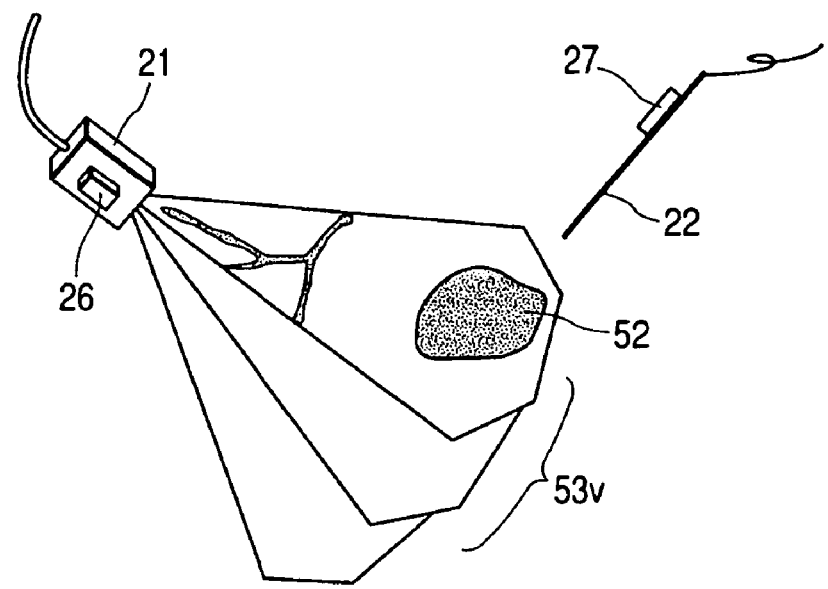
FIGS. 11A and 11B are schematic drawings showing the retrieval and the display of a therapeutic target part in a 1-6 embodiment.
Figure 11B:
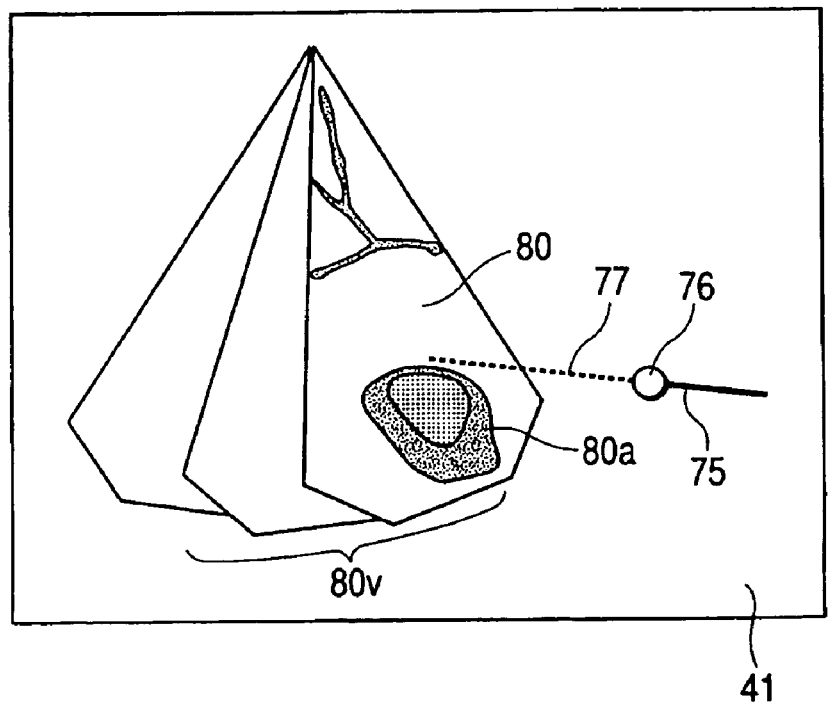

FIGS. 11A and 11B show a situation in which three-dimensional scanning in this embodiment is made in the insertion of a puncture probe without the puncture adaptor shown in FIG. 5 and a display example. An ultrasonic probe in this embodiment shown in FIG. 11A is the mechanical three-dimensional ultrasonic probe or the electronic three-dimensional ultrasonic probe and a position sensor A 26 for detecting the position of the ultrasonic probe and the direction of the central axis of three-dimensional scanning is provided to the ultrasonic probe. The three-dimensional ultrasonic probe 21 mechanically or electronically scans three-dimensionally and acquires the three-dimensional tomographic image data of scanning volume 53v.

When the puncture probe 22 provided with a position sensor 27 is inserted toward a tumor 52 in the scanning volume 53v, the relative positional information managed by a system of a scanned sectional image, probe position/orientation information by the position sensor 26, the relative positional information of a sectional image scanned by the position sensor 26 and puncture probe position/contour information by the position sensor 27 are detected and operated/calculated by the position sensor receiver 25, CPU 15 and the image construction device 18 respectively shown in FIG. 1. These are converted to position/orientation information related to a predetermined origin to be a criterion and as shown in FIGS. 6A to 6F, relative positional relation between the probe and a layer can be displayed.

FIG. 11B is a schematic drawing in which respective tomographic images acquired by the three-dimensional ultrasonic probe are displayed as shown in FIG. 6E and the tomographic layers changing one after another by a three-dimensional scanning system of the three-dimensional ultrasonic probe are displayed on the monitor 32. That is, the three-dimensional ultrasonographic image data is the tomographic image data of plural tomographic images 80 shown in FIG. 6F, in FIG. 11B, a three-dimensional volume display image 80v after the reconstruction of the three-dimensional ultrasonographic image data is displayed and an image of a tumor 80a is displayed in it. Further, in the ultrasonotomographic image, a puncture probe display image 75, a probe end mark 76 and a puncture probe insertion estimated path 77 which is an extended part are displayed.

The three-dimensional ultrasonographic image data in this embodiment can be similarly applied to any tomographic image data described in the 1-1 to 1-5 embodiments.

According to this embodiment, as an internal organ, a tumor to be treated and a cauterized or punctured part can be observed as a real-time three-dimensional image, effect that the determination of a part to be treated, the insertion and the positioning of the puncture probe and the check of a situation after treatment are extremely facilitated is produced.

2-1 Embodiment

Figure 12:
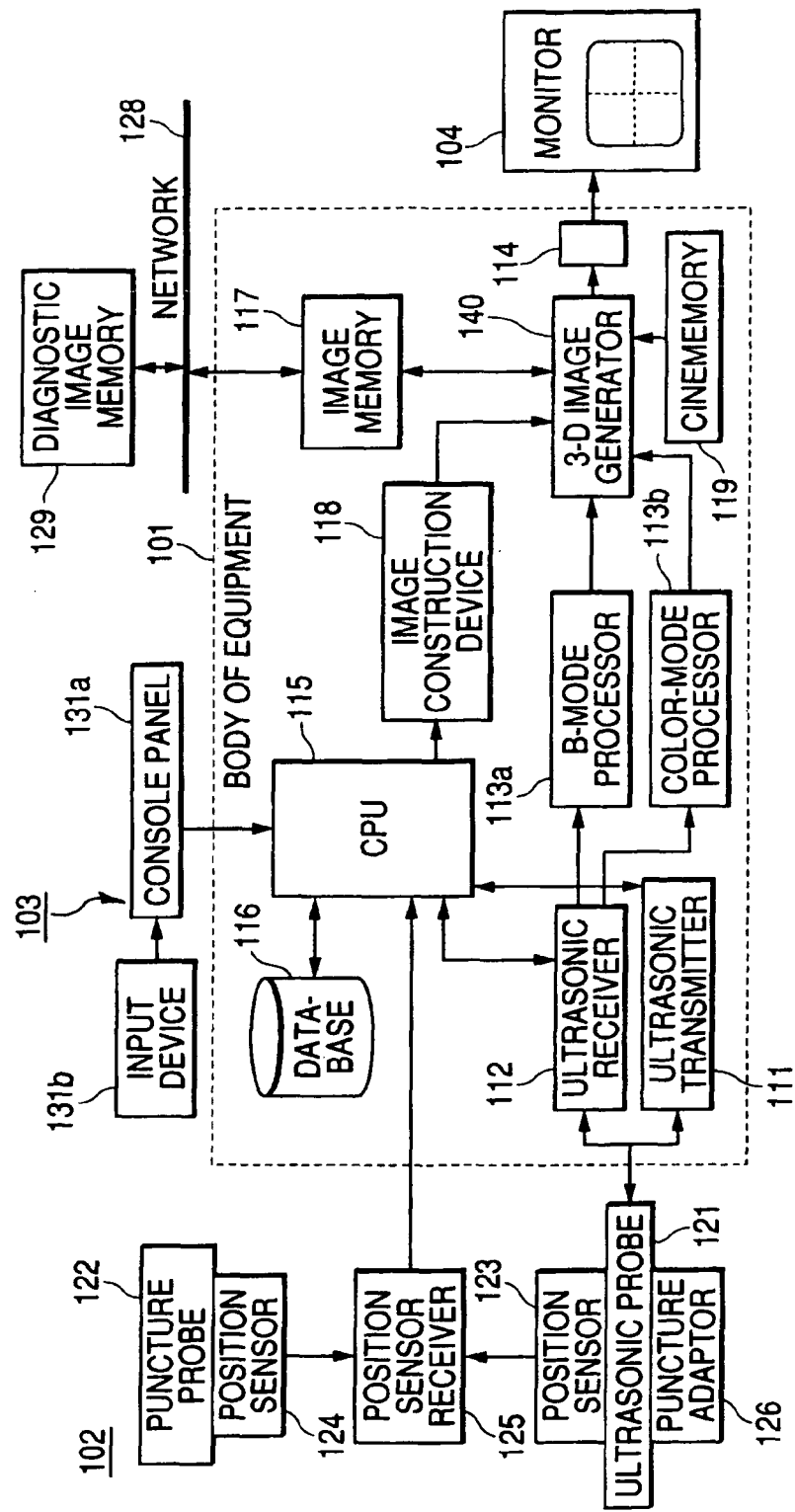
FIG. 12 shows an example of the configuration of ultrasonic diagnostic equipment equivalent to a 2-1 embodiment of the invention.

FIG. 12 shows an example of the configuration of a 2-1 embodiment of the invention. As shown in FIG. 12, ultrasonic diagnostic equipment is composed of the body 101 of the equipment that processes an ultrasonic signal and outputs a picture signal, a puncture/probe section 102 including a puncture adaptor, an ultrasonic probe respectively provided with a position sensor and their receiver, an input controller 103 that controls the body 101 of the equipment and a monitor 104 that displays a picture signal.

The body 101 of the equipment is composed of an ultrasonic transmitter 111, an ultrasonic receiver 112, a B mode processor 113a, a color mode processor 113b, a three-dimensional image generator 140, a display output device 114, CPU 115 for control and operation, a database 116, an image memory 117, an image construction device 118 and a cinememory 119 that stores a dynamic image. The puncture/probe section 102 is composed of the ultrasonic probe 121, a puncture probe 122, a position sensor 123 attached to the ultrasonic probe 121, a position sensor 124 attached to the puncture probe, the position sensor receiver 125 that receives the position and the direction of the probes detected by the position sensors 123, 124 and outputs them to CPU 115 and a puncture adaptor 126 provided to the ultrasonic probe 121 so that the puncture adaptor can be detached.

The input controller 103 that controls the body 101 of the equipment is composed of a console panel 131a provided with function keys for selecting a function and instructing operation, an input device 131b such as a keyboard and a trackball and a fixing/release button 131c.

While the fixing/release button 131c is pressed, the end of the puncture probe is fixed to a specific position on the screen, typically the center of an image display area. When the puncture probe is moved while the fixing/release button 131c is pressed, the end is fixed to the center of the image display area, and an image and the background are moved according to the motion of the puncture probe.

In case a puncture probe for cautery by a radio wave is used for the puncture probe 22, cautery equipment (not shown) for driving a high-frequency radiation electrode of the puncture probe is provided.

FIG. 12 will be described again. An ultrasonic driving signal is transmitted to the connected ultrasonic probe 121 from the ultrasonic transmitter 111 in the body 101 of the equipment, ultrasound is transmitted from an array transducer of the ultrasonic probe 121, and a reflected wave received by the transducer is received and processed by the ultrasonic receiver 112. Tomographic image data processed by the ultrasonic receiver 112 is input to CPU 115. According to the tomographic image data and input via the input device 131b, input for setting a function is made on the console panel 131a, three-dimensional data such as uniform motion, conformal rotation and a position detected by the position sensor 123 is calculated by CPU 115 and is processed in the three-dimensional image generator 140, and a three-dimensional ultrasonographic picture signal is output to the display output device 114. An ultrasonotomographic image is displayed on the screen of the monitor 104 based upon the signal and the stereoscopic observation of an internal organ and a tumor of an examined body is enabled.

The output of the ultrasonic receiver 112 is processed to be tomographic image data for delineating a contour in the B mode processor 113a or to be tomographic image data for delineating blood flow by an ultrasonic Doppler method in the color mode processor 113b, that is, is processed to be ultrasonotomographic image data corresponding to a display mode, and is input to the three-dimensional image generator 140. Therefore, on the monitor 104, a two-dimensional tomographic image or a three-dimensional volume image can be displayed based upon individual ultrasonotomographic image data.

In the body 101 of the equipment, system control is made by CPU 115, temporally continuous plural tomographic image data are stored in the cinememory 119, are continuously regenerated and a dynamic image is displayed on the monitor 104. In the meantime, a tomographic image can be referred to any time by storing individual tomographic image data in the image memory 117, reading it and displaying it on the screen of the monitor 104. Further, diagnostic image data such as an ultrasonotomographic diagnostic image, a CT diagnostic image and an MRI diagnostic image respectively acquired in another medical department from a diagnostic imaging device 129 via an in-hospital network 128 is temporarily stored in the image memory 117, is read and can be displayed on the monitor 104.

The position sensor 124 installed on the puncture probe is provided on the side of the puncture adaptor 126 and can also detect the displacement and an insertion angle of the puncture probe detected by the puncture adaptor.

Figure 13:
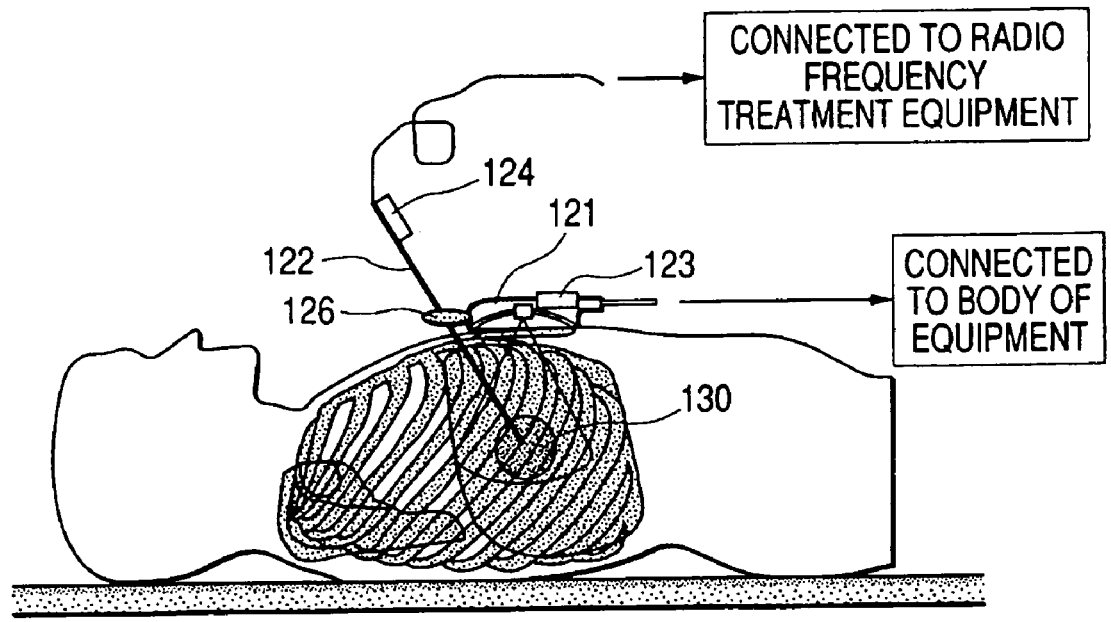
FIG. 13 is an explanatory drawing for explaining relation among an examined body, an ultrasonic probe and a puncture probe when the ultrasonic diagnostic equipment equivalent to the 2-1 embodiment is used.

FIG. 13 shows relation among an example body, the ultrasonic probe 121, the puncture probe 122 and the position sensors 123, 124 installed on the probes. The ultrasonic probe 121 is equipped with the position sensor 123 and the puncture adaptor 126, the position sensor 124 is installed on the puncture probe 122, and the puncture probe 122 is inserted into a therapeutic part 130 of the examined body, being guided by the puncture adaptor 126. The ultrasonic probe 121 is connected to the body 101 of the equipment and the puncture probe 122 is connected to radio frequency treatment equipment via a lead wire.

The six-axis coordinates of the ultrasonic probe 121 in coordinate space, that is, three-axis coordinates of the x-, y- and z-axes and each value of the rotation angle of each axis are detected by the position sensor receiver 125. For example, space having a position in which the position sensor receiver 125 is installed as an origin is called first coordinate space.

Data detected by the position sensor receiver 125 is input to CPU 115 as probe directional data and three-dimensional data in a slice direction of a tomographic image caught by the ultrasonic probe 121 is provided.

In the meantime, the six-axis coordinates in the first coordinate space of the puncture probe 122 are detected by the position sensor receiver 125 via the position sensor 124 installed on the puncture probe 122, and the data of the position and an insertion direction of the puncture probe 122 is input to CPU 115.

For the position sensors 123, 124 used in the 2-1 embodiment, the ones normally equipped for an ultrasonic probe and a puncture probe used for puncture treatment may be also used.

In the database 116 in the body 101 of the equipment, various setting data are stored. For example, the database stores data such as the specifications (the king and an insertion angle of applicable puncture probes) of the puncture adaptor 126 installed on the ultrasonic probe 121, the specifications (the diameter and the length) of the inserted puncture probe 122 and further, control system data such as the configuration (a three-dimensional image, a two-dimensional tomographic image, a color Doppler tomographic image and multi-image combination with another modal image, for example, a CT image and an MRI image) instructed via a function key on the console panel 131a of a display image on the monitor 104.

The image construction device 118 reconstructs the first spatial coordinates based upon three-dimensional ultrasonographic data acquired by the three-dimensional scanning of the ultrasonic probe 121 and constructs the MPR display of a desired tomographic layer and a stereoscopic three-dimensional ultrasonographic image. Further, the contour and the position of the puncture probe 122 are operated in CPU 115 based upon positional data by the position sensor 124 and the specification data of the target puncture probe stored in the database 116 and are constructed on the first spatial coordinates as a display image of the puncture probe. The insertion direction of the puncture probe is extrapolated and a puncture path can be displayed.

To facilitate the verification on the screen of the end of the probe in the display image of the puncture probe 122, the diameter of the probe has only to be displayed slightly thicker at higher intensity than that of the body or exaggeratingly. Or the probe end position may be also displayed in the form of a ball and a circle in which it is supposed that the probe end position is displaced because of the flexure of the probe.

As a puncture probe guide is normally provided so that the puncture probe 122 exists in a field of view (a slice) of a tomographic image by the ultrasonic probe 121 in case the puncture adaptor 126 is installed on the ultrasonic probe 121, the puncture probe 122 is inserted into its puncture probe guide and puncture is made, an image acquired by an echo of the puncture probe 122 can be observed in a tomographic image on one screen. Therefore, in puncture utilizing the puncture adaptor, positional data from the respective position sensors 123, 124 are replaced with two-dimensional space (a tomographic image) in a scanning direction of the ultrasonic probe 121 on the first spatial coordinates, the image construction device 118 constructs a so-called one-screen tomographic image and also writes the calculated highlight of the probe end in the puncture probe display image in the tomographic image.

In a display image on the monitor 104, an image acquired by an echo of the puncture probe 122 is included in an original tomographic image acquired from the ultrasonic probe 121 though its reflection intensity is low and a puncture probe display image is displayed together with a real image of the puncture probe 122.

A puncture probe display image in the 2-1 embodiment is written based upon data detected by the position sensor 124 and is different from a conventional type puncture probe display image in which an intrinsic insertion set directional traverse is displayed based upon the preset specification (a preset insertion angle) of a puncture adaptor while a puncture adaptor is used.

When the rotational quantity and the quantity of displacement of the whole set first spatial coordinate system via the input device 131b such as a trackball in the input controller 103 are specified, the image construction device 118 executes processing for altering a bird's-eye position of a three-dimensional ultrasonographic image including a reconstructed puncture probe display image.

The image construction device 118 stores the position coordinate data of the end of the puncture probe 122 at that time when a functions key, "probe end marking" of the console panel 131a is pressed, writes data for displaying "a probe end mark" having a predetermined contour on the stored position coordinates of the probe end to image data such as a three-dimensional ultrasonographic image and a tomographic image, and displays "the probe end mark" on the monitor 104 together with the ultrasonographic image.

The position coordinate data is also stored after the puncture probe 122 is extracted, however, it is deleted by an instruction, "probe end database deletion".

The image construction device 118 sets second coordinate space having the stored position coordinate data of the probe end as an origin to be a criterion by pressing a function key, "probe end mark relative display" on the console panel 131a after the above-mentioned "probe end marking". The image construction device converts the ultrasonographic image data in the first coordinate space to that in the set second coordinate space. The converted relative position is reconstructed on the second spatial coordinates and an ultrasonographic image is constructed.

Further, the contour and the position of the puncture probe 122 are converted to those in a relative position related to probe end position coordinate data based upon positional data by the position sensor 124 and the specifications of the target puncture probe in the database 116 in CPU 115 and they are constructed on the second spatial coordinates as a puncture probe display image. The highlighting of the probe end in the puncture probe display image is similar to that in the abovementioned case.

The position of the probe in a displayed image is set as the position of an origin to be a criterion by operating a trackball for example of the input device 131*b* by pressing a function key, "origin setting" of the console panel 131*a* in place of the stored position coordinate data of the probe end, and the second coordinate space is set. The display positions of an ultrasonographic image and an image of the puncture probe can be freely changed by designating the position of the origin as described above.

When a function key, "probe end relative display" is pressed on the console panel 131*a*, the contour and the position of the puncture probe 122 are calculated in CPU 115 based upon positional data in the first coordinate space by the position sensor 124 and detected by the position sensor receiver 125 every moment and the specification data of the target puncture probe in the database 116. The calculated data is input to the image construction device 118 and third coordinate space having the momentary position coordinate data of the end of the puncture probe as an origin to be a criterion is set.

Further, ultrasonographic image data in the first coordinate space is converted to that in a relative position related to the momentary position coordinate data of the probe end, is reconstructed on the third spatial coordinates and an ultrasonographic image is constructed.

It need scarcely be said that the contour and the position of the puncture probe 122 the end of which is an origin to be a criterion are also constructed as a puncture probe display image on the third spatial coordinates and this is the fixed data of a puncture probe display image. A puncture probe display image constructed on the third spatial coordinates and a tomographic image are displayed on the monitor 104.

Figure 19:
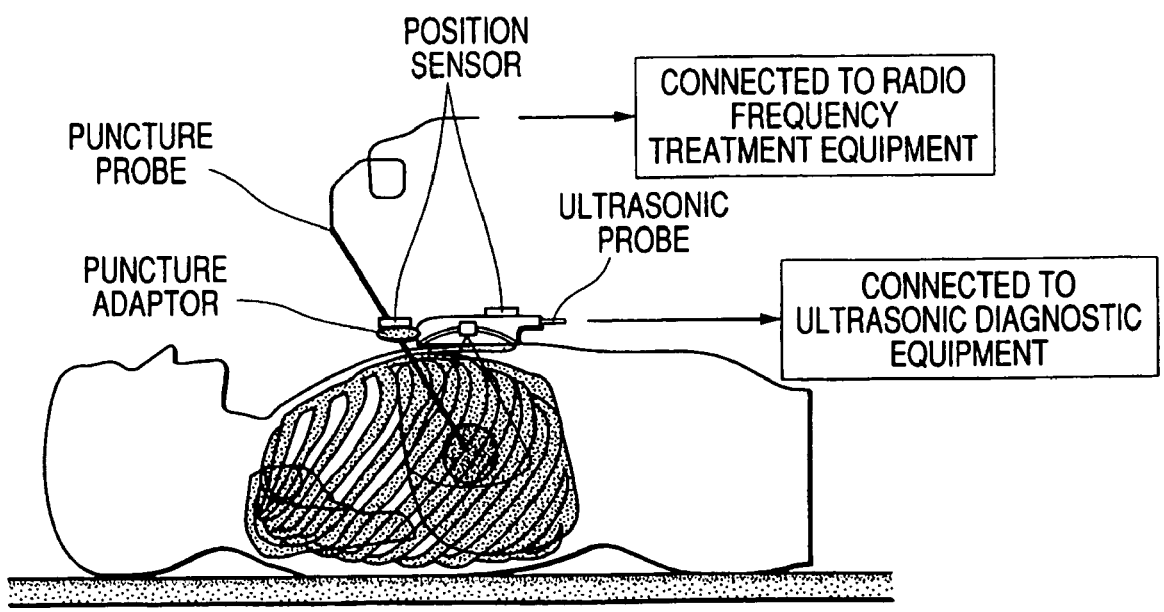
FIG. 19 is an explanatory drawing for explaining relation among an examined body, an ultrasonic probe and a puncture probe when ultrasonic diagnostic equipment equivalent to the 2-2 embodiment is used.

FIG. 19 is a schematic drawing showing a state in which the position sensor for detecting the positional information of the puncture probe is installed on the puncture adaptor installed on the probe.

In the 2-1 embodiment of the invention, the position at the end of the puncture probe and a virtual insertion direction are calculated by the two position sensors 123, 124 installed on the ultrasonic probe 121 and the puncture probe 122 and their tomographic image is displayed.

Figure 16:
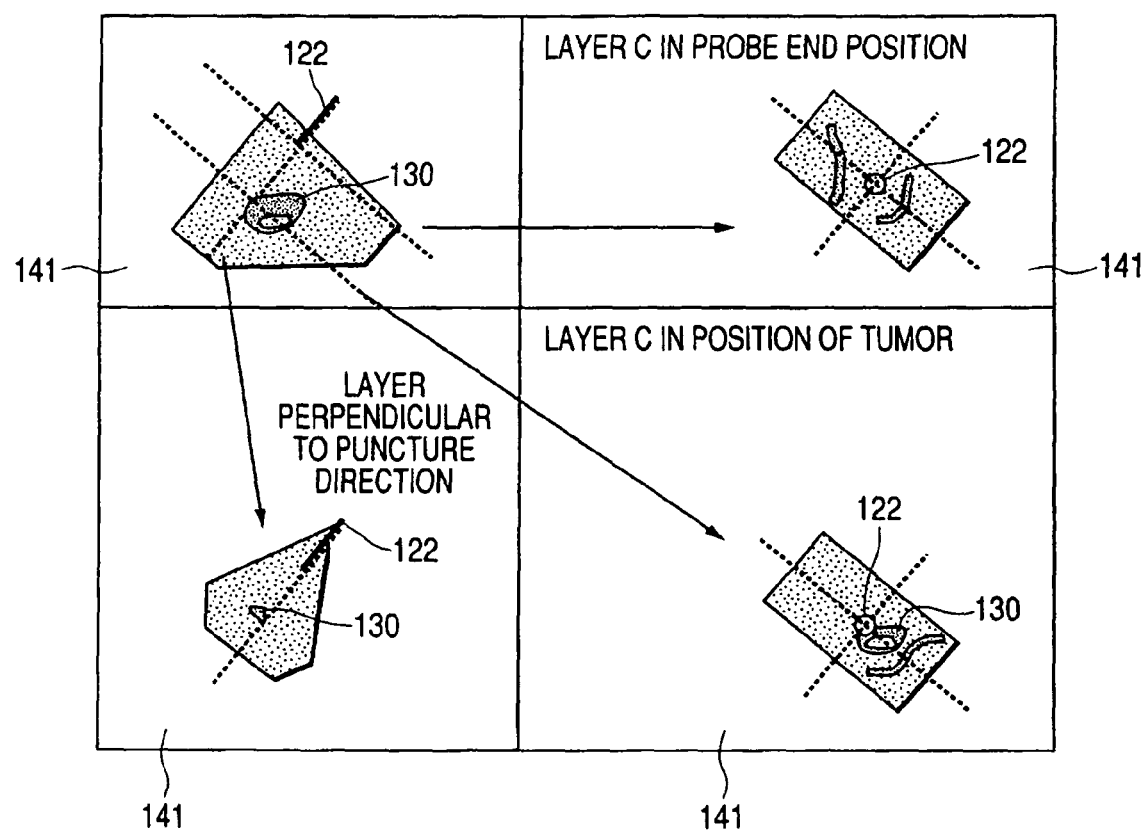
FIG. 16 shows an example of screen display in the 2-1 embodiment of the invention.

In the 2-1 embodiment, four types of tomographic images are displayed on the screen of the monitor 104. First, on the left upside as shown in FIG. 16, a basic tomographic image including a target part such as a liver tumor is displayed and a user can arbitrarily set a layer position for the basic layer of the tomographic image. On the left downside of the monitor screen, an orthogonal tomographic image including an estimated puncture path of the puncture probe 122 is displayed at real time together with the puncture path of the puncture probe 122.

On the tomographic image on the left upside of the screen, a layer is set so that the layer passes the maximum diameter of the liver tumor for example and a tomographic image of a layer orthogonal with the puncture path and also orthogonal with the basic layer on the left upside is displayed on the right downside of the screen.

On the right upside of the screen, a layer including a probe end position and orthogonal with the puncture path and also orthogonal with the basic layer displayed on the left upside is displayed together with the calculated information of the probe end position from the two position sensors.

A principle in which an orthogonal tomographic image in the probe end position is constructed by these position sensors 123, 124 in the 2-1 embodiment will be described below. The following operation is executed in CPU 115 mainly shown in FIG. 12 and reconstruction is executed in the image construction device 118.

Figure 14:
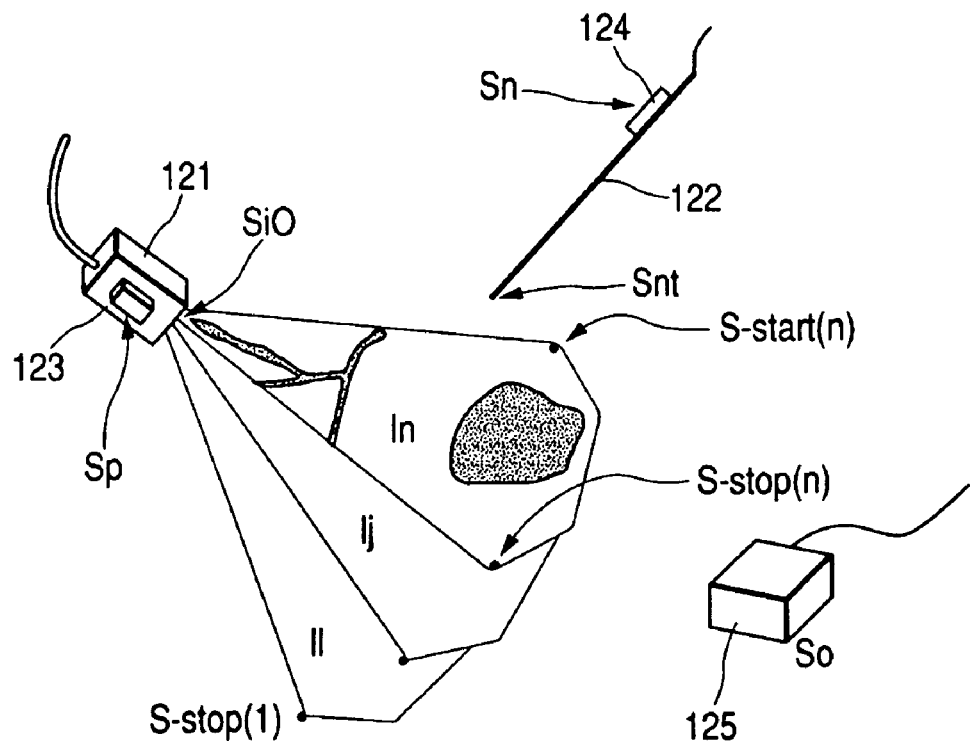
FIG. 14 is an explanatory drawing for explaining three-dimensional ultrasonographic data collection by a two-dimensional array type probe according to sector scanning and the detection of positional relation between the puncture probe and a display image by position sensors 23, 24 in this embodiment.

As shown in FIG. 14, three-dimensional scanning by ultrasound is executed by a sector scan so that a sector-type two-dimensional scan is made sequentially in a slice direction. S0 is set as an origin as a criterion of the coordinates of the position sensor receiver 125. The position sensors 123, 124 provided to the ultrasonic probe 121 and the puncture prove 122 are installed in the vicinity of each grip. The position and the orientation of the position sensor 123 having the position sensor receiver 125 as a criterion and calculated by the position sensor 123 installed on the ultrasonic probe 121 are set as Sp, and the position and the orientation of the position sensor 124 having the position sensor receiver 125 as a criterion and calculated by the position sensor 124 installed on the puncture probe 122 are set as Sn. The end position of the puncture probe is set as Snt and the center of a probe surface position for a sector scan by the ultrasonic probe 121 is set as Si0 as an origin of an image.

Scanning by the ultrasonic diagnostic equipment is two-dimensionally executed in a sector type ordinarily having the origin Si0 of an image as a criterion. Each of n pieces of tomographic images acquired in the slice direction by this scan is I1, I2, I3, - - - , In.

The position of a "j"th ($1 \leq j \leq n$) image (Ij) is defined by the following three points.

Origin of image; Si0
Deepest position of scan start raster of image; S-start (j)
Deepest position of scan stop raster of image; S-stop (j)

In three-dimensional scanning by the ultrasonic diagnostic equipment, volume encircled by the following five points is scanned.

Origin of image; Si0
Deepest position of scan start raster of first image; S-start (1)
Deepest position of scan stop raster of first image; S-stop (1)
Deepest position of scan start raster of "n"th image; S-start (n)
Deepest position of scan stop raster of "n"th image; S-stop (n)

Figure 15:
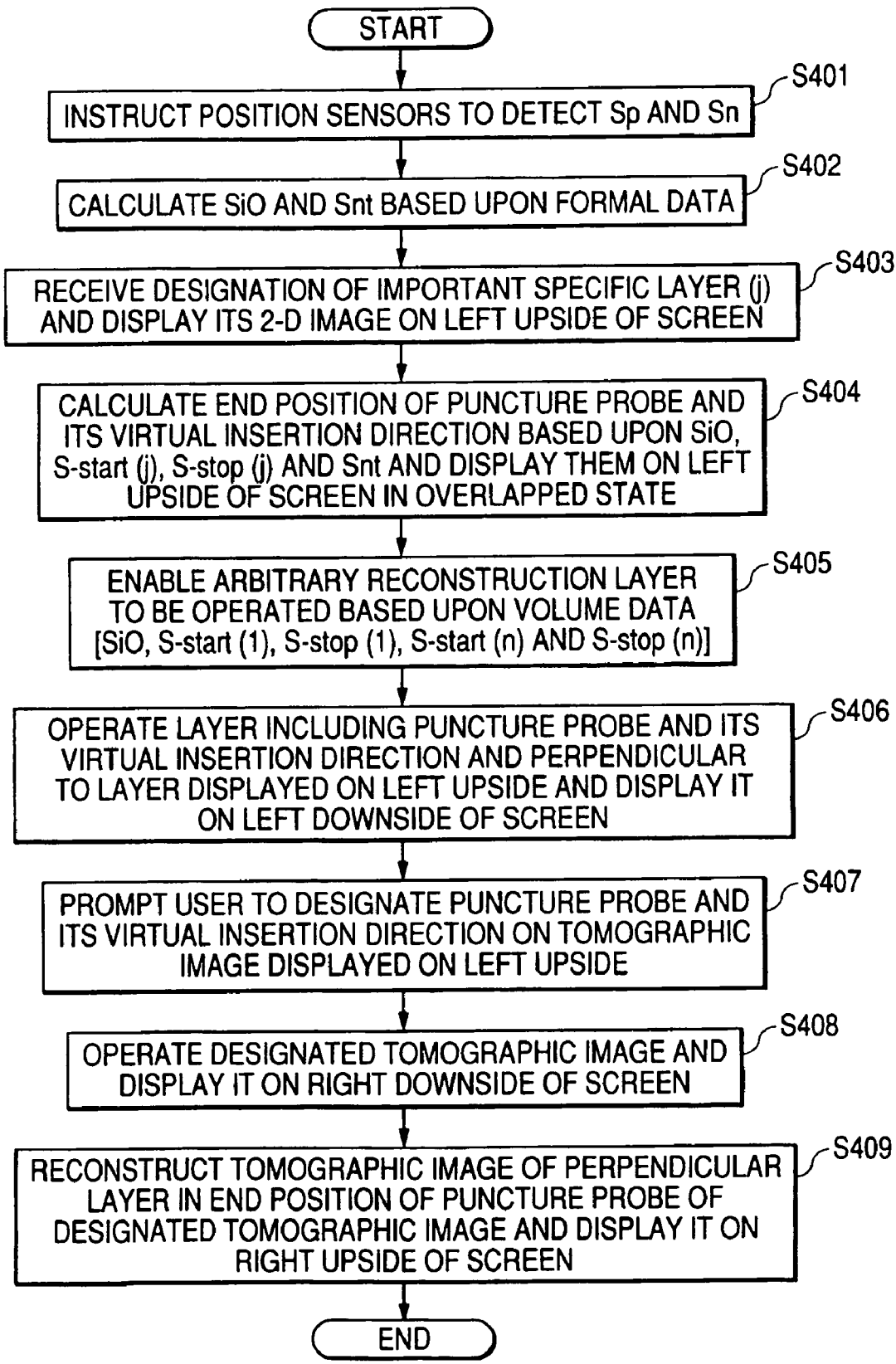
FIG. 15 is a flowchart for explaining the flow of processing in the 2-1 embodiment of the invention.

Next, referring to FIG. 15 showing a flowchart and FIG. 16 showing a display state on the screen, algorithm for interlocking a scanned layer and display based upon the positional information of the end of the puncture probe 122 acquired by the position sensors 123, 124 will be described below.

First, in a step S401, the positions Sp, Sn of the ultrasonic probe and the puncture probe are detected by each position sensor 123, 124. In the next step S402, the origin Si0 of an image and the position Snt of the end of the puncture probe are calculated based upon each contour data of the ultrasonic probe 121 and the puncture probe 122.

Next, in a step S403, when a layer including a clinically important target part such as a tumor, for example a "j"th layer is designated beforehand, an image of the layer is two-dimensionally displayed on the left upside of the screen as shown in FIG. 16.

In the next step S404, the puncture probe and the probe end position are displayed as shown by a black full line on the left upside in FIG. 16 based upon the positional information of the "j"th layer, that is, the origin Si0 of the image, the deepest position S-start (j) of the scan start raster of the "j"th image, the deepest position S-stop (j) of the scan stop raster of the "j"th image and the positional information Snt of the end of the puncture probe 122. Further, as shown by a black broken line on the left upside in FIG. 16, a virtual insertion direction of the puncture probe 122 is displayed.

In the next step S405, an arbitrary layer can be operated for reconstruction based upon volume data encircled by the following five points, that is, the origin Si0 of the image, the deepest position S-start (1) of the scan start raster of a first image, the deepest position S-stop (1) of the scan stop raster of the first image, the deepest position S-start (n) of the scan start raster of an "n"th image and the deepest position S-stop (n) of the scan stop raster of the "n"th image.

Therefore, in the next step S406, a tomographic image of a layer orthogonal with the layer displayed on the left upside in FIG. 16 including the puncture probe 122 and the virtual insertion direction of the puncture probe is operated and is displayed on the left downside of the screen as shown in FIG. 16. In a step S407, on the tomographic image on the left upside of the screen displayed as shown in FIG. 16, a user can designate an arbitrary puncture probe and its virtual insertion direction and in a step S408, as shown on the right downside of the screen in FIG. 16, a tomographic image designated by the user is operated and the operated tomographic image is displayed.

When the end of the puncture probe 122 is pointed by the user on the left upside of the screen in FIG. 16, a tomographic image of an orthogonal layer (a layer C) in the probe end position in the insertion direction of the puncture probe 122 in the designated tomographic image is operated for reconstruction and is displayed as shown on the right upside of the screen in FIG. 16 in the next step S409.

The 2-1 embodiment has an advantage that not only a tomographic image in an orthogonal direction with the puncture probe in the position at the end of the puncture probe but a tomographic image including an insertion direction of the puncture probe and a therapeutic part for treatment by puncture, a tomographic image perpendicular to the tomographic image, a tomographic image orthogonal with the insertion direction of the puncture probe in the therapeutic part and others can be viewed at a time. The embodiment also has an advantage that these tomographic images vary and are displayed at real time according to the motion of the puncture probe when it is moved. Besides, this embodiment has an advantage that the user can set the tomographic image including the therapeutic part on the layer orthogonal with the insertion direction of the puncture probe and others on the basic tomographic image displayed on the left upside of the screen of the monitor 104.

In the 2-1 embodiment, an orthogonal tomographic image is calculated based upon ultrasonic volume data calculated based upon an inserted position and an insertion direction of the puncture probe by the two position sensors installed on the ultrasonic probe and the puncture probe and is displayed. Next, referring to the drawings, a 2-2 embodiment of the invention further provided with a third position sensor will be described.

2-2 Embodiment

Figure 17:
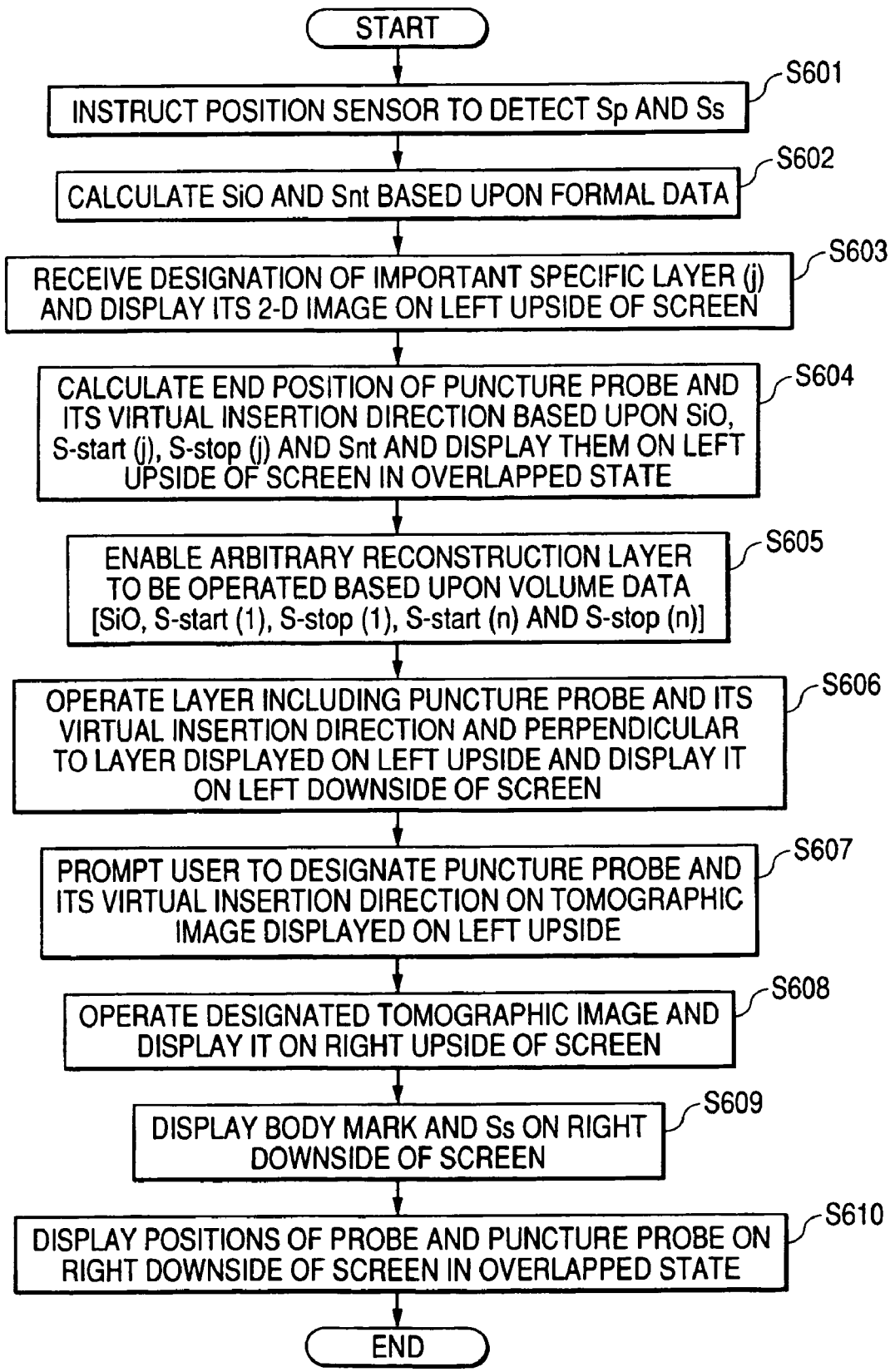
FIG. 17 is a flowchart for explaining the flow of processing in a 2-2 embodiment of the invention.
Figure 18:
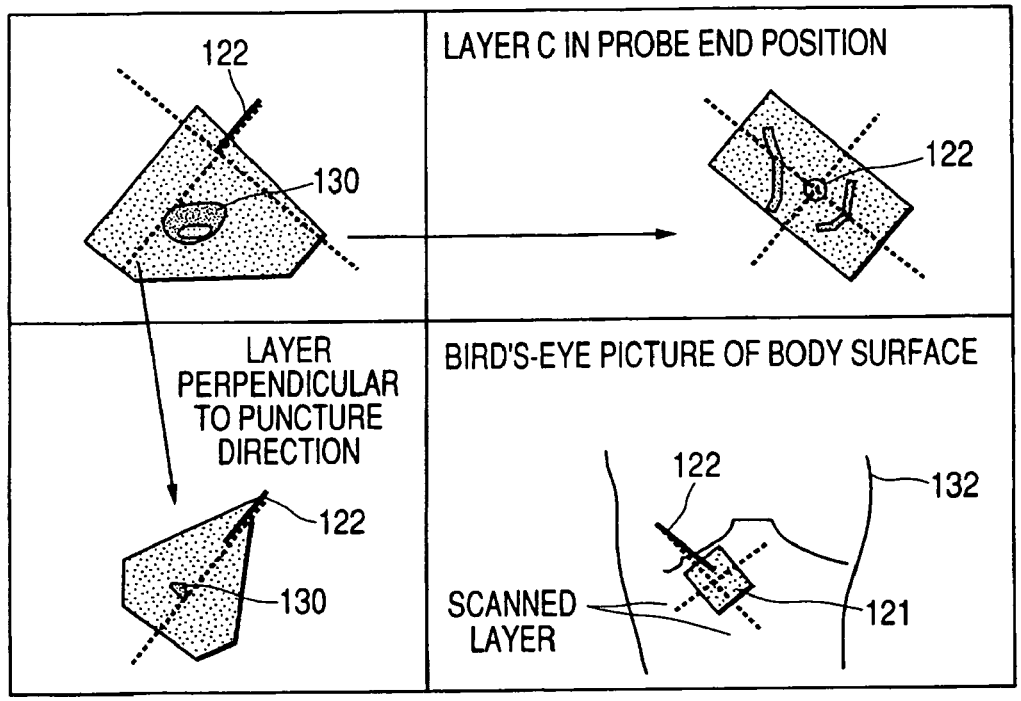
FIG. 18 shows an example of screen display in the 2-2 embodiment of the invention.

FIG. 17 shows the flow of processing in a 2-2 embodiment and FIG. 18 shows an example of the screen displayed on a monitor 104. In this embodiment, a third position sensor (the position shall be Ss) is installed in a suitable location on the surface of an examined body, for example on a pit of the stomach and positional relation between an ultrasonic probe and a puncture probe can be also grasped based upon the axis of the body.

On the left upside of the screen shown in FIG. 18, a basic tomographic image including a liver tumor, the puncture probe and its insertion direction is displayed and on the left downside, an orthogonal tomographic image including an estimated path of the puncture probe is displayed interlocking with the puncture path of the puncture probe at real time. In the meantime, on the right upside of the screen, a tomographic image including the probe end position, orthogonal with the puncture path and also orthogonal with the basic tomographic image is displayed interlocking with the real-time end position information of the puncture probe calculated by position sensors 123, 124.

The scan of the basic tomographic image displayed on the left upside of the screen is controlled so that the probe end position is ordinarily included and the tomographic image displayed on the right upside is displayed at real time according to the end position of the displaced puncture probe.

On the right downside of the screen, a body mark is displayed, positional information from the surface of the body is added by the position sensor installed on the surface of the body, and positional relation between the ultrasonic probe and the puncture probe from a view point over the surface of the body is displayed.

Referring to FIG. 17, the flow of processing for such display in the 2-2 embodiment will be described below. First, in a step S601, the position Sp of the ultrasonic probe, the position Sn of the puncture probe and the position Ss of the pit of the stomach are detected and in the next step S602, an origin Si0 of an image and the position Snt at the end of the puncture probe are calculated based upon the contour data of the ultrasonic probe and the puncture probe.

In a step S603, a layer including a clinically important part such as a tumor, for example, a "j"th layer is designated beforehand and as shown on the left upside in FIG. 18, its tomographic image is two-dimensionally displayed. Next, in a step S604, the puncture probe and the probe end position are displayed as shown by a black full line on the left upside in FIG. 18 based upon the positional information of the "j"th layer, that is, the origin Si0 of the image, the deepest position S-start (j) of the scan start raster of the "j"th image, the deepest position S-stop (j) of the scan stop raster of the "j"th image and the positional information Snt of the end of the puncture probe 122. Further, as shown by a black broken line on the left upside in FIG. 18, a virtual insertion direction of the puncture probe 122 is displayed.

In the next step S605, an arbitrary layer can be operated for reconstruction based upon volume data encircled by the following five points, that is, the origin Si0 of the image, the deepest position S-start (1) of the scan start raster of a first image, the deepest position S-stop (1) of the scan stop raster of the first image, the deepest position S-start (n) of the scan start raster of an "n"th image and the deepest position S-stop (n) of the scan stop raster of the "n"th image.

Therefore, in the next step S606, a tomographic image of a layer orthogonal with the layer displayed on the left upside in FIG. 16 and including the puncture probe 122 and a virtual insertion direction of the puncture probe is operated and is displayed on the left downside of the screen as shown in FIG. 16.

In a step S607, on the basic tomographic image on the left upside of the screen displayed as shown in FIG. 18, a user can designate an arbitrary puncture probe and its virtual insertion direction and when the end of the puncture probe 122 is pointed on the left upside of the screen shown in FIG. 18 by the user, a tomographic image of an orthogonal layer (a layer C) in the probe end position in the insertion direction of the puncture probe 122 on the designated tomographic image as shown on the right upside of the screen shown in FIG. 16 is operated for reconstruction in the next step S608 and is displayed.

In the next step S609, a body mark registered beforehand, for example, a body mark 132 in the abdomen in a state in which a patient lies on the back is displayed on the right downside of the screen. A three-dimensional image generator 140 generates an image in which a mark 121 of the ultrasonic probe and a mark 122 of the puncture probe on the examined body are arranged on the body mark 132 based upon the position of the surface detected by the position sensor installed on the surface of the examined body, the detected position and direction of the ultrasonic probe 121 and the detected position and direction of the puncture probe 122.

The user designates the installed position of the third position sensor installed on the surface of the body, in this case, the pit of the stomach and a direction of the axis of the body on the body mark 132. As the position Sp of the ultrasonic probe, the position Sn of the puncture probe and the position Ss of the pit of the stomach are known by the three position sensors, correspondence is formed between the body mark 132 on the screen and the position Ss of the pit of the stomach by pointing on the body mark 132. Therefore, in a step S610, as shown on the right downside in FIG. 18, the position of the ultrasonic probe and the position of the puncture probe can be schematically displayed according to each positional information.

As according to this embodiment of the invention, the positional relation of the ultrasonic probe and the puncture probe with the axis of the body is displayed from a view point over the surface of the body, the embodiment has an advantage that a doctor who performs treatment by puncture depending upon the ultrasonic diagnostic equipment can more easily judge how the ultrasonic probe and the puncture probe are to be operated.

Figure 20A:
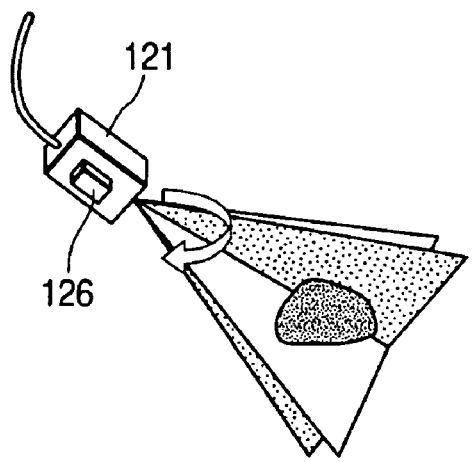
FIG. 20A shows an example of a mechanical rotary sector probe and FIG. 20B shows an example of a mechanical gate scanning sector probe in the 2-2 embodiment.
Figure 20B:
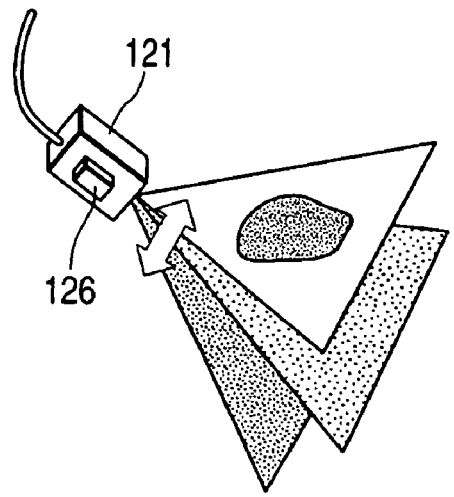

For a method of three-dimensionally collecting ultrasonographic image data, a method except a method of making a sector scan in a slice direction by a two-dimensional array probe as shown in FIG. 14 may be also adopted. In FIG. 20A, a method of mechanically rotating a sector-type tomographic image by a one-dimensional array probe is shown and in FIG. 20B, a method of mechanically displacing a sector-type tomographic image by the one-dimensional array probe in the slice direction is shown.

Figure 21:
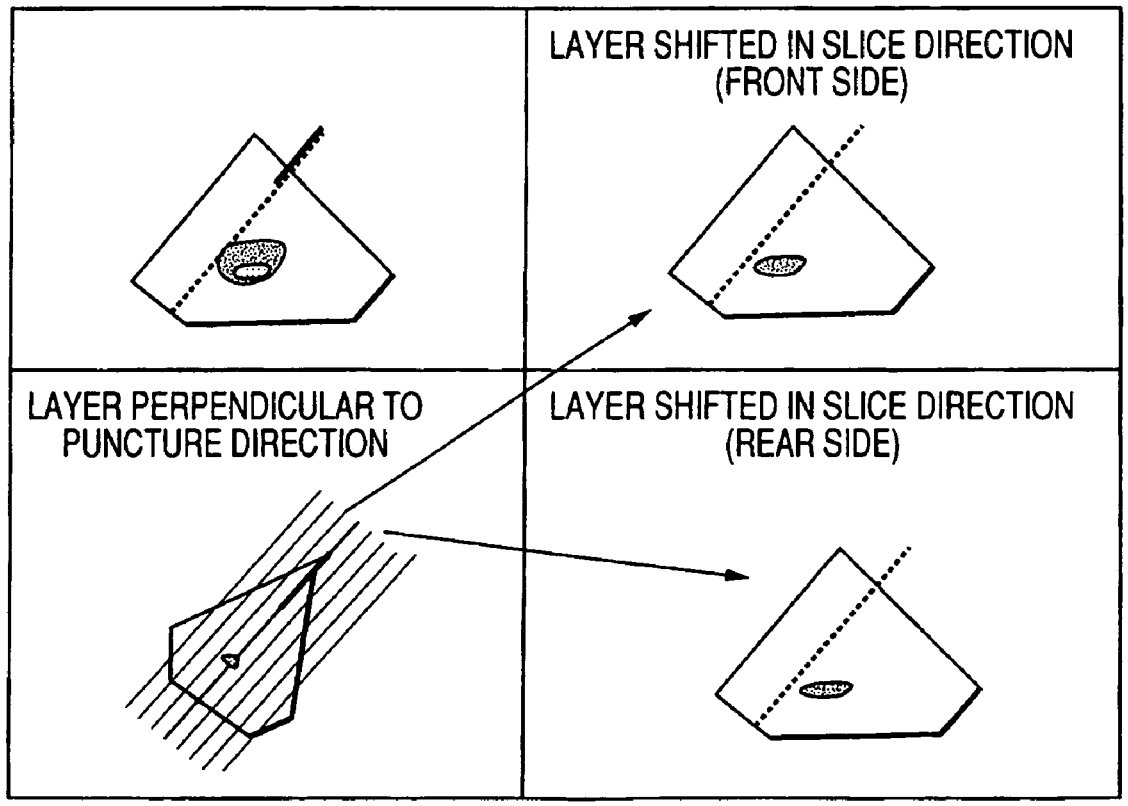
FIG. 21 shows an example of screen display in a transformed example of this embodiment.

FIG. 21 shows a transformed example of the display mode shown in FIG. 16. Tomographic images acquired by displacing a basic tomographic image shown on the left upside in FIG. 21 by desired pith in the slice direction in parallel are displayed on the right upside and on the right downside in FIG. 21.

On the left downside in FIG. 21, an orthogonal layer in a puncture direction with the basic tomographic image is displayed. Further, the positions of the tomographic images acquired by displacing the basic tomographic image by desired pitch in the slice direction in parallel are displayed by full lines. The number of tomographic images displaced in parallel is not limited to two, may be also three or more, and the number of tomographic images displaced in parallel and displayed is also not limited to two.

Figure 22:
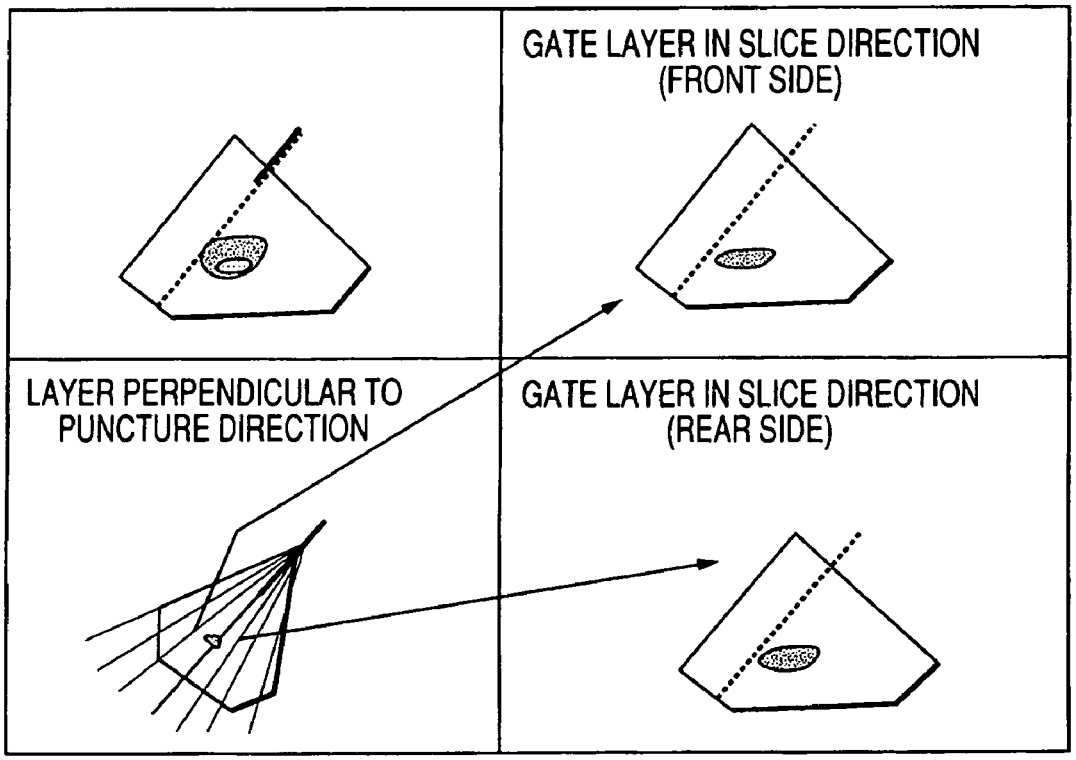
FIG. 22 shows an example of screen display in a transformed example of this embodiment.

FIG. 22 shows a second transformed example of the display mode shown in FIG. 16. Tomographic images acquired by displacing a basic tomographic image shown on the left upside in FIG. 22 by desired angular pitch in the slice direction are displayed on the right upside and on the right downside in FIG. 22. On the left downside in FIG. 22, an orthogonal layer with the basic tomographic image in a direction of puncture is displayed. Further, the positions of the tomographic images acquired by displacing the basic tomographic image by the desired angular pitch in the slice direction are displayed by full lines. The number of gate tomographic layers is not limited to two, may be also three or more, and the number of displayed gate tomographic images is also not limited to two.

2-3 Embodiment

Figure 23:
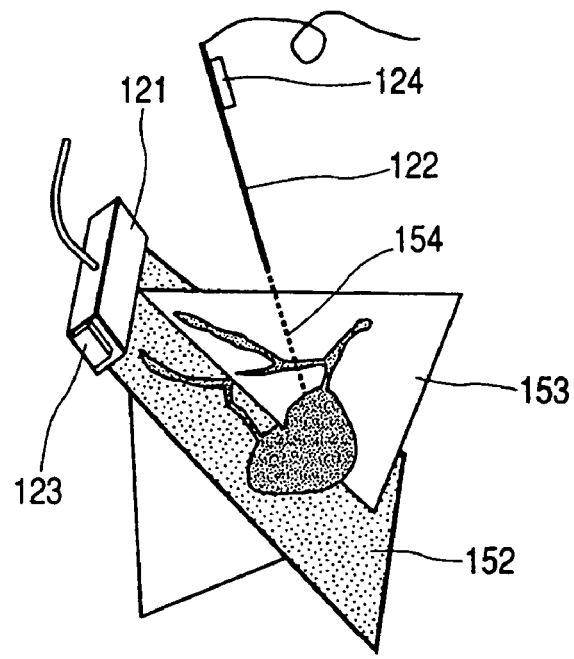
FIG. 23 shows an embodiment by a two-dimensional linear array probe in this embodiment.

Referring to FIG. 23, a 2-3 embodiment of the invention will be described below. An electronic linear two-dimensional array probe provided with plural ultrasonic transducers arrayed in a matrix is utilized. A linear two-dimensional scan is possible and simultaneously, a beam can be deflected in a sector in a slice direction. A puncture path of a puncture probe for an ultrasonic probe can be detected by position sensors 123, 124. As shown in FIG. 23, ultrasonic diagnostic equipment recognizes the puncture path and scans to acquire tomographic images including the puncture path. On a tomographic layer including the puncture path, a puncture probe insertion estimated path 154 is displayed as shown by a broken line in FIG. 23. The enhancement of a frame rate and the improvement of the quality of an image are enabled by forming only a two-dimensional image of the puncture path without a three-dimensional scan.

CPU 115, a transmitter 111 and a receiver 112 control the transmission/reception of the ultrasonic probe 121 based upon the detected position and direction of the ultrasonic probe 121 and the detected position and direction of the puncture probe 122 to scan a layer 153 including the puncture probe 122 or the insertion estimated path 154 or a layer in the vicinity by ultrasound.

Besides, CPU 115, the transmitter 111 and the receiver 112 control the transmission/reception of the ultrasonic probe 121 based upon the detected position and direction of the ultrasonic probe 121 and the detected position and direction of the puncture probe 122 to scan a layer 152 crossed with the end of the puncture probe 122 or the insertion estimated path 154, typically orthogonal by ultrasound.

Figure 24:
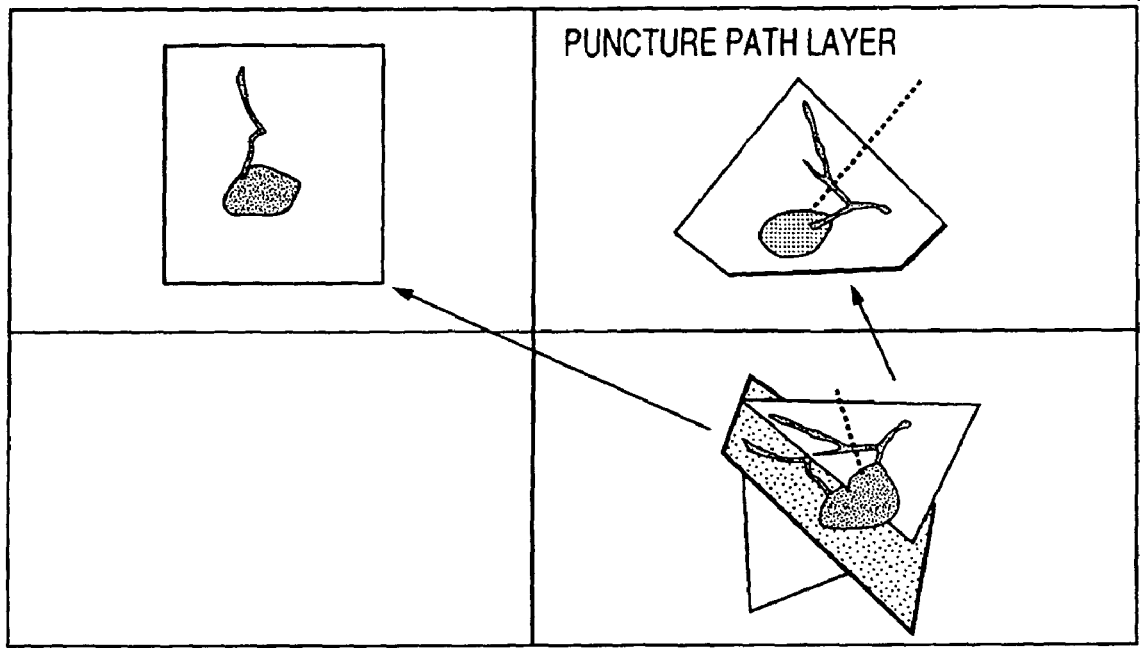
FIG. 24 shows an example of screen display in a transformed example of this embodiment.

FIG. 24 shows a display example in case the scan shown in FIG. 23 is executed. On the left upside, a basic image (a linear image) is shown and on the right upside, a tomographic layer including a puncture path is shown.

Figure 25:
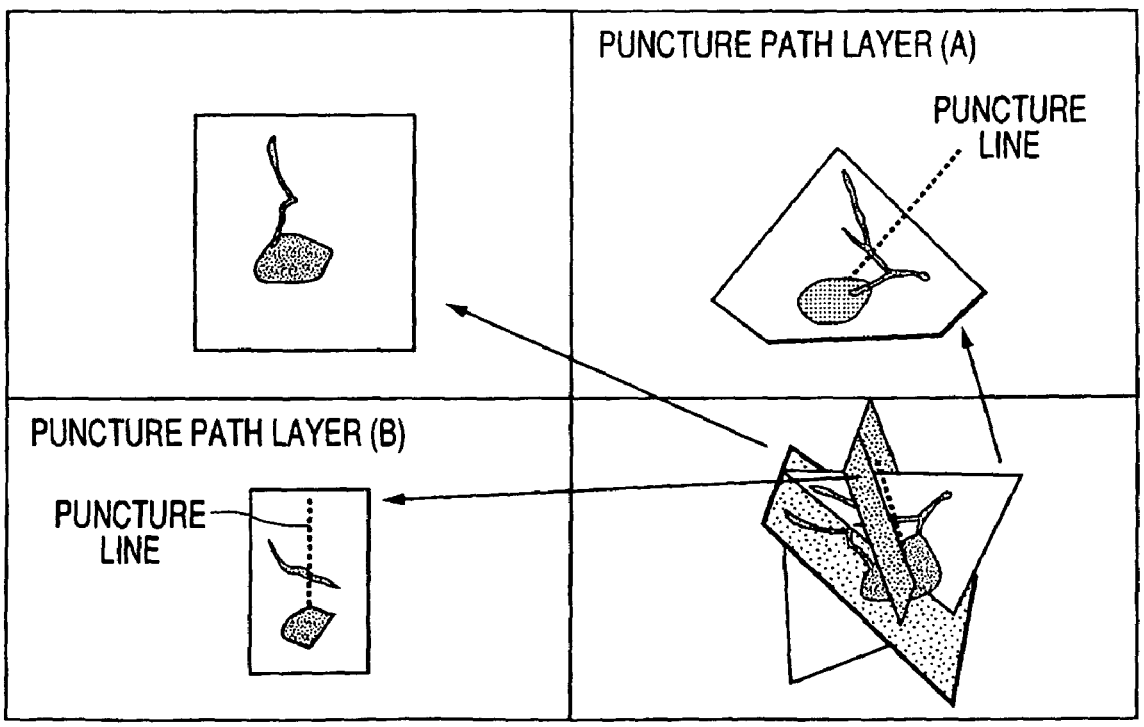
FIG. 25 shows an example of screen display in a transformed example of this embodiment.

FIG. 25 further explains the display of an orthogonal layer with a two-dimensional image of a puncture path. Hereby, the displacement of the puncture probe from the estimated path because of flexure and others can be observed.

The invention is not limited to the above-mentioned 2-1, 2-2 and 2-3 embodiments and within a range in which the key points are not changed, various transformations and combinations are possible. The scan mode of the probe is not limited to a sector type and a linear mode. For the scan mode in the vicinity of the puncture path, the transformation of various scan modes including the puncture path is possible. For example, in the above-mentioned embodiments, the processing for reconstructing based upon three-dimensional volume data is executed by CPU of the ultrasonic diagnostic equipment and the examples of the storage in the image memory are described, however, the similar processing and storage can be also executed by an external workstation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Ultrasonic diagnostic equipment, comprising:
an ultrasonic probe that transmits and receives ultrasound to and from, respectively, an examined body to perform three-dimensional scanning to generate three-dimensional volume image data;
a first probe position sensor that detects the position and the direction of the ultrasonic probe;
an image generator that generates image data based upon the output of the ultrasonic probe;
a puncture probe, separate from the ultrasonic probe, to be inserted into an examined body;
a second probe position sensor that detects the position and the direction of the puncture probe inserted into the examined body;
a position sensing receiver that receives the detected position and direction of the puncture probe from the second probe position sensor;
a CPU in communication with the position sensing receiver and configured to convert the detected position and direction of the puncture probe to a relative position of an end position of the puncture probe;
a display image generator that generates, from the three-dimensional volume image data, data of a two-dimensional display image in which the end position of the puncture probe is displayed, and that, based on a user activation of a fixed display operation, changes a position and orientation of the image along a two-dimensional plane that has been imaged according to a change of orientation and position of the puncture probe along the two-dimensional plane such that the end position of the puncture probe is fixedly displayed, even when the puncture probe is moved in its position and orientation, and independent of movement of the ultrasonic probe, to a specific position in an image display area according to the detected position and direction of the ultrasonic probe and the detected position and direction of the puncture probe based upon the image data; and
a display that displays the display image in the image display area.

2. Ultrasonic diagnostic equipment according to claim 1, wherein:
the display image generator synthesizes a line mark corresponding to the puncture probe and a line mark corresponding to an insertion estimated path of the puncture probe in the display image.

3. Ultrasonic diagnostic equipment according to claim 2, further comprising:
a memory for storing the data of the display image in which the line mark corresponding to the puncture probe and the line mark corresponding to the insertion estimated path of the puncture probe are synthesized.

4. Ultrasonic diagnostic equipment according to claim 3, wherein:
the display image generator synthesizes the stored display image with a tomographic image generated by the image generator at real time and controls display of the synthesized stored display image on the display.

5. Ultrasonic diagnostic equipment according to claim 2, wherein the display image generator synthesizes the line marks such that:
the line mark corresponding to the puncture probe is displayed by a full line; and
the line mark corresponding to the insertion estimated path of the puncture probe is displayed by a dotted line or a broken line.

6. Ultrasonic diagnostic equipment according to claim 2, wherein the display image generator synthesizes the line marks such that:
a position in which the line mark corresponding to the puncture probe is crossed with the display image is displayed in a contour or hue different from a position in which the line mark corresponding to the insertion estimated path of the puncture probe is crossed with the display image.

7. Ultrasonic diagnostic equipment according to claim 2, wherein the display image generator synthesizes the line marks such that:
the line mark corresponding to the insertion estimated path of the puncture probe is displayed together with estimated path image marks extended at an angle according to the magnitude of displacement in an insertion direction of the puncture probe.

8. Ultrasonic diagnostic equipment according to claim 1, wherein:
the specific position is the center position of the image display area.

9. Ultrasonic diagnostic equipment according to claim 1, wherein:
the first probe position sensor is detachable from the ultrasonic probe.

10. Ultrasonic diagnostic equipment according to claim 1, wherein:
the image generator generates the image data to be data of multilevel tomographic images.

11. Ultrasonic diagnostic equipment according to claim 1, further comprising:
a button for releasing the fixing of the end position of the puncture probe to the specific position in the image display area.

12. Ultrasonic diagnostic equipment according to claim 11, wherein:
the display image generator converts the image data to the data of a two-dimensional image by rendering;
when the fixing is set by the button, the position of a view point of the rendering is displaced so that the end position of the puncture probe is coincident with the specific position in the image display area; and
when the fixing is released by the button, the displacement of the position of the view point of the rendering is stopped.

13. Ultrasonic diagnostic equipment according to claim 1, wherein the display image generator synthesizes the data such that the display image is an image that shows image data corresponding to two sections crossing at the specific position, in a three-dimensional form reflecting a positional relationship between the two sections.

14. Ultrasonic diagnostic equipment, comprising:
an ultrasonic probe that transmits and receives ultrasound to and from, respectively, an examined body to perform three-dimensional scanning to generate three-dimensional volume image data;
an image generator that generates image data based upon the output of the ultrasonic probe;

a puncture probe, separate from the ultrasonic probe, to be inserted into an examined body;

a position specification device including a probe position sensor for acquiring the position of the end of the puncture probe inserted into the examined body;

a position sensing receiver that receives the detected position and direction of the puncture probe from the probe position sensor;

a CPU in communication with the position sensing receiver and configured to convert the detected position and direction of the puncture probe to a relative position of an end position of the puncture probe;

a display image generator that, from the three-dimensional volume image data, calculates a display position of the image data in which the end position of the puncture probe is displayed, and that, based on a user activation of a fixed display operation, changes a position and orientation of the image data along a two-dimensional plane that has been imaged according to a change of orientation and position of the puncture probe along the two-dimensional plane so that the end position of the puncture probe acquired by the position specification device is fixedly displayed, even when the puncture probe is moved in its position and orientation, and independent of movement of the ultrasonic probe, to a specific position in an image display area and generates the data of a two-dimensional display image so that the image data is displayed in the position; and a display for displaying the display image in the image display area.

15. Ultrasonic diagnostic equipment according to claim 14, wherein the display image generator synthesizes the data such that the display image is an image that shows image data corresponding to two sections crossing at the specific position, in a three-dimensional form reflecting a positional relationship between the two sections.

* * * * *